US007125844B2

(12) United States Patent
Fardis et al.

(10) Patent No.: US 7,125,844 B2
(45) Date of Patent: Oct. 24, 2006

(54) DAB[9] DERIVATIVES OF LIPOPEPTIDE ANTIBIOTICS AND METHODS OF MAKING AND USING THE SAME

(75) Inventors: Maria Fardis, San Carlos, CA (US); Dale R. Cameron, Richmond (CA); Vincent A. Boyd, Vancouver (CA)

(73) Assignee: Migenix Inc., Vancouver (CA)

( * ) Notice: Subject to any disclaimer, the term of this patent is extended or adjusted under 35 U.S.C. 154(b) by 355 days.

(21) Appl. No.: 10/336,641

(22) Filed: Jan. 2, 2003

(65) Prior Publication Data
US 2004/0138107 A1 Jul. 15, 2004

Related U.S. Application Data

(60) Provisional application No. 60/453,710, filed on Jan. 3, 2002.

(51) Int. Cl.
*A61K 38/00* (2006.01)
(52) U.S. Cl. ......................................................... 514/9
(58) Field of Classification Search ................ 514/9
See application file for complete search history.

(56) References Cited

U.S. PATENT DOCUMENTS

| | | | | |
|---|---|---|---|---|
| 3,057,779 A | 10/1962 | Shay et al. | ................... | 167/65 |
| 3,160,561 A | 12/1964 | Shibata et al. | ................ | 167/65 |
| 3,639,582 A | 2/1972 | Umezawa et al. | .......... | 424/118 |
| 3,781,420 A | 12/1973 | Nishimura et al. | ......... | 424/118 |
| 3,817,973 A | 6/1974 | Bouchaudon et al. | .... | 260/112.5 |
| 4,524,135 A | 6/1985 | Abbott et al. | ................. | 435/69 |
| 4,977,083 A | 12/1990 | Boeck | ........................ | 435/71.3 |
| 4,994,270 A | 2/1991 | Boeck et al. | ............... | 424/118 |
| 5,028,590 A | 7/1991 | Fukuda et al. | ................ | 514/11 |
| 5,039,789 A | 8/1991 | Fukuda et al. | ................ | 530/317 |
| 5,629,288 A | 5/1997 | Lattrell et al. | ................. | 514/9 |
| 5,912,226 A | 6/1999 | Baker et al. | ................... | 514/9 |
| 6,146,872 A | 11/2000 | Ueda et al. | ................. | 435/231 |
| 6,194,383 B1 | 2/2001 | Hammann et al. | ............ | 514/11 |
| 6,716,962 B1 | 4/2004 | Borders et al. | ............ | 530/317 |
| 2002/0028771 A1* | 3/2002 | Curran et al. | .................. | 514/9 |

FOREIGN PATENT DOCUMENTS

| | | |
|---|---|---|
| EP | 629636 B1 | 12/1998 |
| WO | WO 99/43700 | 9/1999 |
| WO | WO 02/05837 | 1/2002 |

OTHER PUBLICATIONS

Vertesy, et al "Friulimicins: Novel Lipopeptide Antibiotics with Peptidoglycan Synthesis Inhibiting Activity from Actinoplanes friulliensis sp. nov. II. Isolation and Structural Characterization," The Journal of Antibiotics 53(8): 816-827, Aug. 2000.*
Bodanszky, M. et al., "Structure of the Peptide Antibiotic Amphomycin," *Journal of the American Chemical Society* 95(7): 2352-2357, Apr. 4, 1973.
Boeck, L.D. et al., "Deacylation of A21978C, an Acidic Lipopeptide Antibiotic Complex, By *Actinoplanes utahensis,*" *The Journal of Antibiotics* 41(8): 1085-1092, Aug. 1988.
Debono, M. et al., "Enzymatic and Chemical Modifications of Lipopeptide Antibiotic A21978C: The Synthesis and Evaluation of Daptomycim (LY146032)," *The Journal of Antibiotics* 41(8): 1093-1105, Aug. 1988.
Fujino, M., "On Glumamycin, a New Antibiotic. VI. An Approach to the Amino Acid Sequence," *Bulletin of the Chemical Society of Japan* 38(4): 517-522, 1965.
Hausmann, W.K. et al., "Structure Determination of Fatty Acids from the Antibiotic Aspartocin," in *Antimicrobial Agents and Chemotherapy—1963*, Proceeding of the Third Interscience Conference on Antimicrobial Agents and Chemotherapy, Sylvester, J.C. (ed.), American Society for Microbiology, 1963, pp. 352-359.
Hausmann, W.K. et al., "α, β-Diaminobutyric Acid Obtained from Aspartocin," *The Journal of Antibiotics* 22(5): 207-210, May 1969.
Heinemann, B. et al., "Amphomycin, A New Antibiotic," *Antibiotics and Chemotherapy* 3: 1239-1242, 1953.
Hinuma, Y., "Zaomycin, A New Antibiotic from a *Streptomyces* sp.," *The Journal of Antibiotics, Ser. A* 7(4): 134-136, Aug. 1954.
Huber, F.M. et al., "The formation of daptomycin by supplying decanoic acid to *Strptomyces roseosporus* cultures producing the antibiotice complex A21978C," *Journal of Biotechnology* 7(4): 283-292, 1988.
Martin and Hausmann, "Isolation and Identification of D-α-Pepecolic Acid, α[L],β-Methylaspartic Acid and α,β-Diaminobutyric Acid from the Polypeptide Antibiotic Aspartocin," *Journal of the American Chemical Society* 82: 2079, Apr. 20, 1960.
Naganawa, H. et al., "A Novel Fatty Acid from Laspartomycin," *The Journal of Antibiotics* 23(8): 423-424, Aug. 1970.
Naganawa, H. et al., "Laspartomycin, A New Anti-Staphylococcal Peptide," *The Journal of Antibiotics* 21(1): 55-62, Jan. 1968.
Shay, A.J. et al., "Aspartocin. I. Production, Isolation, and Characteristics," *Antibiotics Annual 1959-1960*, pp. 194-198.
Shoji, J-I et al., "Studies on Tsushimycin. I. Isolation and Characterization of an acidic acylpeptide containing a new fatty acid," *The Journal of Antibiotics* 21(7): 439-443, Jul. 1968.
Vértesy, L. et al., "Friulimicins: Novel Lipopeptide Antibiotics with Peptidoglycan Synthesis Inhibiting Activity from *Actinoplanes friuliensis* sp. nov. II. Isolation and Structural Characterization," *The Journal of Antibiotics* 53(8): 816-827, Aug. 2000.

* cited by examiner

*Primary Examiner*—Bruce R. Campell
*Assistant Examiner*—Thomas S. Heard
(74) *Attorney, Agent, or Firm*—Darby & Darby PC

(57) ABSTRACT

The present invention provides Dab[9] derivatives of amphomycin-type lipopeptide antibiotics that display antimicrobial activity against Gram-positive bacteria, methods and intermediates for synthesizing such compounds, and methods of using the compounds in a variety of contexts, including in the treatment and prevention of infections.

25 Claims, 1 Drawing Sheet

DAB⁹ DERIVATIVES OF LIPOPEPTIDE ANTIBIOTICS AND METHODS OF MAKING AND USING THE SAME

BACKGROUND OF THE INVENTION

1. Field of the Invention

The present invention relates generally to derivatives of lipopeptide antibiotics of the amphomycin type, methods and intermediates for their preparation and methods for their use as pharmacologically active substances, in particular against infections caused by Gram-positive bacteria.

2. Description of the Related Art

Secondary metabolites from microorganisms are successfully employed for the treatment of infectious diseases. Secondary metabolites are low molecular weight compounds produced by "biosynthetic one-way streets" which branch off from the primary metabolism. The function of the secondary metabolites for the particular producer is unclear. To date, about 8000 secondary metabolites isolated from cultures of various microorganisms (especially fungi and bacteria of the genus *Streptomyces*) are known.

These secondary metabolites are mainly used to treat infectious diseases. One important class of such secondary metabolites is the amphomycin-type lipopeptide antibiotics. The amphomycin-type lipopeptide antibiotics display their antibiotic activity against Gram-positive bacteria, such as, for example, *Streptococci*, *Staphylococci* and *Enterococci* and consist of a macrocyclic peptide "core" acylated at its N-terminus with a lipophilic fatty acid. The amphomycin-type antibiotics are generally produced as mixtures of compounds that differ with respect to the structures of their macrocyclic peptide cores and/or their fatty acid moieties. Examples of such amphomycin-type lipopeptide antibiotics include: amphomycin (glumamycin) Heinemann et al., 1953, *Antibiot. Chemother.* 3:1239–1242; Fujino et al., 1965, *Bull. Chem. Soc. Jap.* 38:515; Bodanszky et al., 1973, *J. Am. Chem. Soc.* 95:2352; Shibata et al., U.S. Pat. No. 3,160,561); aspartocin (Shay et al., U.S. Pat. No. 3,057,779; Shay et al., 1960, *Antibiotics Ann.* 194; Hausman et al., 1964, *Antimicrob. Ag. Chemother.* 352; Hausman et al., 1969, *J. Antibiotics* 22:207; Martin et al., 1960, *J. Am. Chem. Soc.* 2079); crystallomycin (Gauze et al., 1957, *Antibiotiki* 2:9–14); antibiotic A1437 (Hammann et al., EP 0 629 636 B1; Hammann et al., U.S. Pat. No. 6,194,383; Lattrell et al., U.S. Pat. No. 5,629,288); friulimycin (Vertesy et al., 2000, *J. Antibiotics* 53:816); tsushimycin (Shoji et al., 1968, *J. Antibiotics* 21:439; Nishimura et al., U.S. Pat. No. 3,781,420); and zaomycin (Hinuma, 1954, *J. Antibiotics* 7(4):134–136; Kuroya, 1960, *Antibiotics Ann.* 194; Kuroya, JP 8150).

Owing in part to the wide spread use of antibiotic therapies, many strains of bacteria have developed resistance to these and other classes of antibiotic compounds. Strains of the genera *Streptococcus*, *Staphylococcus*, and *Enterococcus* are proving to be particularly problematic organisms to control efficiently because of developed resistance to conventional antibiotics (for example β-lactam antibiotics and/or glycopeptide antibiotics such as, for example, vancomycin and teicoplanin). Another group of microorganism strains that have developed resistance include the methicillin-resistant *Staphylococcus aureus* strains ("MRSA" strains). It is now known that these MRSA strains are often resistance to other antibiotics (for example, quinolones) in addition to methicillin.

Given the rampant rise of strains of microorganisms that are resistant to current antibiotic therapies, there is a continuous need for the development of novel antibiotics and antibiotics with novel mechanisms of action. The present invention meets such needs, and further provides other related advantages.

BRIEF SUMMARY OF THE INVENTION

In one aspect, the present invention provides novel lipopeptide antibiotics of the amphomycin type. The novel antibiotics consist of an amphomycin-type macrocyclic peptide "core," and a lipophilic fatty acid moiety or a lipophilic fragment. The macrocyclic peptide core includes a Dab residue, or other amino acid having a side chain with a primary amine group or an amino acid or a lipophilic fragment, and derivatives thereof, which is typically at the 9-position of the macrocycle ("Dab⁹ residue"). The macrocyclic peptide core also includes an exocyclic amino acid, which is typically Asp or Asn, which intervenes the cyclic portion of the core and the lipophilic fatty acid moiety. The β-amino group of the macrocyclic Dab⁹ residue is acylated with a substituent that includes a primary or secondary amine or an amino acid or a lipophilic fragment, and derivatives thereof. In one embodiment, this amine-containing substituent is an amino acid, typically an α-, β- or γ-amino acid. The amino acid may optionally include one or more side-chain moieties, for example, a side chain of one of the twenty genetically encoded amino acids. The lipophilic fatty acid moiety is linked to the N-terminus of the macrocyclic peptide core via its terminal carboxyl group. The lipophilic fatty acid moiety may be a linear or branched, saturated or singly or multiply unsaturated fatty acid or hydroxy fatty acid with a chain length of from 6 to 22 carbon atoms. In another embodiment, the N-terminus of the macrocyclic peptide core is linked to a lipophilic fragment, wherein the lipophilic fragment is selected from the group consisting of hydrogen, ($C_1$–$C_{25}$) alkyl optionally substituted with one or more of the same or different $R^{15}$ groups, ($C_1$–$C_{25}$) heteroalkyl optionally substituted with one or more of the same or different $R^{15}$ groups, ($C_5$–$C_{10}$) aryl optionally substituted with one or more of the same or different $R^{15}$ groups, ($C_5$–$C_{15}$) arylaryl optionally substituted with one or more of the same or different $R^{15}$ groups, ($C_5$–$C_{15}$) biaryl optionally substituted with one or more of the same or different $R^{15}$ groups, 5–10 membered heteroaryl optionally substituted with one or more of the same or different $R^{15}$ groups, ($C_6$–$C_{26}$) arylalkyl optionally substituted with one or more of the same or different $R^{15}$ groups and 6–26 membered heteroarylalkyl optionally substituted with one or more of the same or different $R^{15}$ groups; each $R^{15}$ is independently selected from the group consisting of —$OR^{16}$, —$SR^{16}$, $NR_{16}R^{16}$, —CN, —$NO_2$, —$N_3$, —C(O)$OR^{16}$, —C(O)$NR^{16}R^{16}$, —C(S)$NR^{16}R^{16}$, —C($NR^{16}$)$NR^{16}R^{16}$, —CHO, —$R^{16}$CO, —$SO_2R^{16}$, —$SO_2R^{16}$, —PO($OR^{16}$)$_2$, —PO($OR^{16}$), —$CO_2H$, —$SO_3H$, —$PO_3H$, halogen and trihalomethyl; and each $R^{16}$ is independently selected from the group consisting of hydrogen, $(C_1–C_6)$ alkyl, $(C_5–C_{10})$ aryl, 5–10 membered heteroaryl, $(C_6–C_{16})$ arylalkyl and 6–16 membered heteroarylalkyl.

As will be described in more detail in connection with methods of synthesizing the compounds, the compounds of the invention may be structurally pure, or they may be in the form of a composition comprising a mixture of one or more structurally different compounds. They may also be in the form of free acids or bases or in the form of salts, such as pharmaceutically acceptable salts.

In another aspect, the present invention provides compositions comprising the compounds of the invention. Generally, the compositions comprise one or more compounds of the invention and an appropriate carrier, excipient or diluent. The exact nature of the carrier, excipient or diluent will depend upon the desired use for the composition, and may range from being suitable or acceptable for environmental uses, to being suitable or acceptable for veterinary uses, to being suitable or acceptable for human use (i.e., pharmaceutically acceptable).

In still another aspect, the present invention provides methods of synthesizing the compounds of the invention. In one embodiment, the compounds of the invention may be prepared from a parent amphomycin-type lipopeptide antibiotic isolated from culture by reacting the parent antibiotic with an appropriately protected reagent, such as an appropriately protected amino acid, under conditions suitable for attaching the reagent to the β-nitrogen of the macrocyclic $Dab^9$ residue. Any protecting groups present may then be removed to yield a $Dab^9$ derivative of the invention.

Typically, such parent antibiotics are mixtures of compounds that differ from one another with respect to the structures of their macrocyclic peptide cores and/or fatty acid moieties or lipophilic fragments. In this instance, the resultant $Dab^9$ derivatives of the invention are obtained as mixtures of compounds, the structures and relative quantities of which are dictated by the structures and relative quantities of the compounds comprising the parent antibiotic mixture. When structurally pure compounds of the invention are desired, the component compounds comprising the parent antibiotic mixture may be separated and isolated from one another before derivatization of the macrocyclic $Dab^9$ residue. Alternatively, the separation and isolation may be carried out on the resultant product of the $Dab^9$ derivatization reaction, either before or after removal of any protecting groups, to yield structurally pure $Dab^9$ derivatives of the invention.

In many cases, the structures of the fatty acid moieties of the parent antibiotics are unknown. $Dab^9$ derivatives of the invention having precisely defined fatty acids or lipophilic fragments may be obtained by removing the lipophilic fatty acid moiety and replacing it with a fatty acid or lipophilic fragment having a specified structure. In one embodiment, the parent antibiotic mixture is delipidated to yield a delipidated intermediate and this delipidated intermediate is then reacted with the desired fatty acid under acylating conditions to yield a synthetic antibiotic having a precisely defined fatty acid moiety. This synthetic antibiotic may then be derivatized according to the methods described above to yield $Dab^9$ derivatives of the invention. As will be recognized by skilled artisans, the β-amino group of the macrocyclic $Dab^9$ residue should be protected with a suitable protecting group prior to delipidation of the parent antibiotic.

In certain embodiments, the fatty acid or lipophilic fragment may be optionally linked to the amino-terminal of the exocyclic amino acid via a linker, wherein said linker may be any kind of chemical functionality that can form a covalent bond with nitrogen known to those of skill in the art. In a exemplary embodiment, $X^1$ is selected from the group consisting of —CO—, —SO$_2$, —CS—, —PO—, —OPO—, —OC(O)—, —NHCO—, —NR$^1$CO—. In another preferable embodiment, $X^1$ is —CO—, —NHCO, or —SO$_2$. In a particularly preferred embodiment, $X^1$ is —CO—. Similarly, the substituents added to generate the $Dab^9$ derivatives may be optionally attached via similar linker and optionally include a spacer moiety. In certain embodiments, the spacer moiety is hydrophilic or hydrophobic, long or short, rigid, semirigid or flexible. In related embodiments, the spacer moiety is an alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, sapcers may include single, double, triple or aromatic carbon-carbon bonds, nitrogen-nitrogen bonds, carbon-nitrogen, carbon-oxygen bonds and/or carbon-sulfur bonds, and may therefor include functionalities such as carbonyls, ethers, thioethers, carboxamides, sulfonamides, ureas, urethanes, hydrazines, and the like.

In instances where all of the component compounds of the particular parent antibiotic mixture share the same macrocyclic peptide core, and differ in structure only with respect to the structures of their fatty acid moieties, structurally pure $Dab^9$ derivatives having a specified fatty acid moiety are obtained. In instances where the component compounds of the parent antibiotic mixture have structurally distinct macrocyclic peptide cores, such as is the case for, e.g., antibiotic A1437, the resultant $Dab^9$ derivatives comprise a mixture of compounds which differ from one another with respect to the structures of their macrocyclic peptide cores. Structurally pure $Dab^9$ derivatives may be obtained from this mixture, if desired, by separating and isolating the component $Dab^9$ derivatives using conventional techniques.

In another embodiment, $Dab^9$ derivatives obtained by derivatizing a parent antibiotic as previously described may be delipidated, typically before removing any present protecting groups, and relipidated with a fatty acid moiety or lipophilic fragment having a specified structure. Removal of any present protecting groups yields a $Dab^9$ derivative of the invention. Whether this resultant $Dab^9$ derivative is structurally pure or comprises a mixture of compounds will depend upon whether the $Dab^9$ preparation used as a starting material for the delipidation is structurally pure with respect to the macrocyclic peptide core.

The above-described synthetic pathways yield novel protected intermediates and these intermediates constitute another aspect of the instant invention.

In still another aspect, the present invention provides methods of inhibiting the growth of microbes, such as Gram-positive bacteria. The method generally involves contacting a microbe with one or more compounds of the invention (or an acceptable salt thereof) in an amount effective to inhibit the growth of the microbe. The method may be practiced to achieve a microbistatic effect where the growth of the microbe is inhibited, or to achieve a microbicidal effect, where the microbe is killed.

In a final aspect, the present invention provides methods for treating and/or preventing microbial infections, such as infections caused by Gram-positive bacteria, in a subject such as human, plant or animal. The methods generally involve administering to a subject one or more compounds or compositions of the invention in an amount effective to treat or prevent the infection. The compounds or compositions may be administered systemically or applied topically, depending on the nature of the infection.

DETAILED DESCRIPTION OF THE INVENTION

Abbreviations

Figure 1:
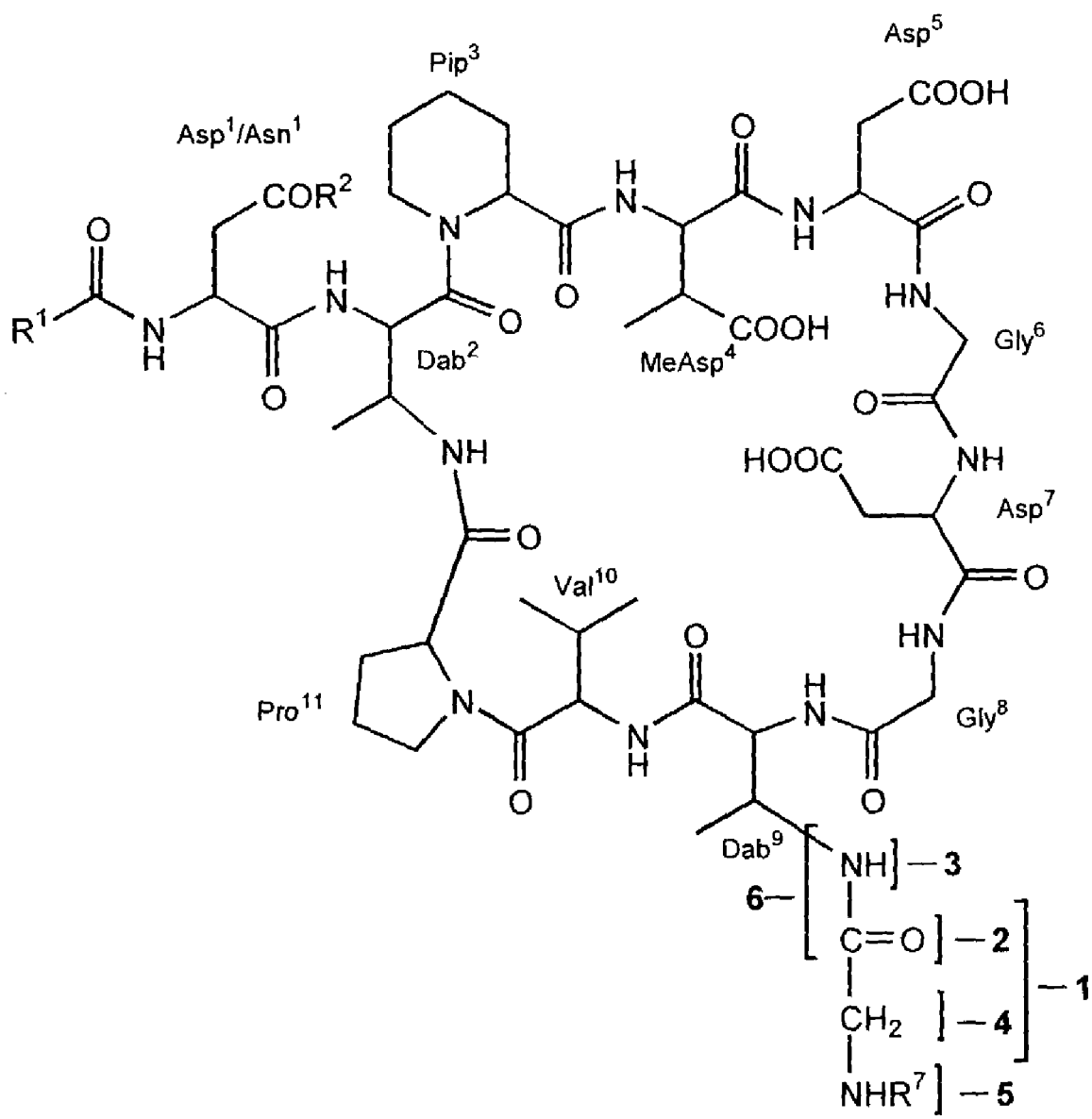
FIG. 1 is an illustration of a $Dab^9$ derivative of the invention.

The abbreviations used for the genetically encoded amino acids and certain common non-encoded amino acids are conventional and are as follows:

| Amino Acid | "Three-Letter" Abbreviation | One-Letter Abbreviation |
| --- | --- | --- |
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| β-methylaspartate | MeAsp | |
| 2,3-diaminobutyric acid | Dab | |
| Pipecolic acid (homoproline) | Pip or hPro | |
| Sarcosine (N-methyl glycine) | Sar or MeGly | |

Unless specified otherwise, amino acids may be in either the D- or L-configuration. As used herein, "ATCC" refers to the American Type Culture Collection, Manassas, Va. 20108 (see also www.atcc.org), and "NRRL" refers to the Agriculture Research Service Culture Collection, Microbial Genomics and Bioprocessing Research Unit, National Center for Agriculture Utilization Research, Peoria, Ill. 61604 (see also nrrl.ncaur.usda.gov).

Definitions

Any concentration or percentage ranges recited herein are to be understood to include concentrations of any integer within the range and fractions thereof, such as one tenth and one hundredth of an integer, unless otherwise indicated. As used herein, "about" or "comprising essentially of" means±15%.

As used herein, the following terms are intended to have the following meanings:

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 4 carbon atoms.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_1$–$C_4$) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is ($C_1$–$C_6$) or ($C_1$–$C_4$) alkyleno. Also preferred are straight-chain saturated alkano groups, e.g., methano, ethano, propano, butano, and the like.

"Heteroalkyl, Heteroalkanyl Heteroalkenyl, Heteroalkanyl, Heteroalkyldiyl and Heteroalkyleno" refer to alkyl, alkanyl, alkenyl, alkynyl, alkyldiyl and alkyleno groups, respectively, in which one or more of the carbon atoms (and any associated hydrogen atoms) are each independently replaced with the same or different heteroatoms or heteroatomic groups. Typical heteroatoms or heteroatomic groups that can be included in these groups include, but are not limited to, —O—, —S—, —Se—, —O—O—, —S—S—, —O—S—, —O—S—O—, —O—NR'—, —NR'—, —NR'—NR'—, =N—N=, —N=N—, —N=N—NR'—, —PH—, —P(O)$_2$—, —O—P(O)$_2$—, —SH$_2$—, —S(O)$_2$—, —SnH$_2$— and the like, and combinations thereof, including, for example, —NR'—S(O)$_2$—, where each R' is independently selected from the group consisting of hydrogen, alkyl, alkanyl, alkenyl, alkynyl, aryl, arylalkyl, heteroaryl and heteroarylalkyl, as defined herein.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$–$C_{14}$) aryl, with ($C_5$–$C_{10}$) being even more preferred. Particularly preferred aryls are cyclopentadienyl, phenyl and naphthyl.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$–$C_{20}$) arylalkyl, e.g., the alkanyl, alkenyl or alkynyl moiety of the arylalkyl group is ($C_1$–$C_6$) and the aryl moiety is ($C_5$–$C_{14}$). In particularly preferred embodiments the arylalkyl group is ($C_6$–$C_{13}$), e.g., the alkanyl, alkenyl or alkynyl moiety of the arylalkyl group is ($C_1$–$C_3$) and the aryl moiety is ($C_5$–$C_{10}$).

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, ∃-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–14 membered heteroaryl, with 5–10 membered heteroaryl being particularly preferred. The most preferred heteroaryl groups are those derived from thiophene, pyrrole, benzothiophene, benzofuran, indole, pyridine, quinoline, imidazole, oxazole and pyrazine.

"Heteroarylalkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heterorylalkynyl is used. In preferred embodiments, the heteroarylalkyl group is a 6–20 membered heteroarylalkyl, e.g., the alkanyl, alkenyl or alkynyl moiety of the heteroarylalkyl is 1–6 membered and the heteroaryl moiety is a 5–14-membered heteroaryl. In particularly preferred embodiments, the heteroarylalkyl is a 6–13 membered heteroarylalkyl, e.g., the alkanyl, alkenyl or alkynyl moiety is 1–3 membered and the heteroaryl moiety is a 5–10 membered heteroaryl.

"Substituted:" refers to a group in which one or more hydrogen atoms are each independently replaced with the same or different substituent(s). Typical substituents include, but are not limited to, —X, —$R^{13}$, —O—, =O, —OR, —$SR^{13}$, —S—, =S, —$NR^{13}R^{13}$, =$NR^{13}$, $CX_3$, —$CF_3$, —CN, —OCN, —SCN, —NO, $NO_2$, =$N_2$, —$N_3$, —$S(O)_2$O—, —$S(O)_2$OH, —$S(O)_2R^{13}$, —$OS(O_2)$O—, —$OS(O)_2$OH, —$OS(O)_2R^{13}$, —$P(O)(O^-)_2$, —$P(O)(OH)(O^-)$, —OP$(O)_2(O^-)$, —$C(O)R^{13}$, —$C(S)R^{13}$, —$C(O)OR^{13}$, —$C(O)O^-$, —$C(S)OR^{13}$, and —$C(NR^{13})NR^{13}R^{13}$, where each X is independently a halogen; each $R^{13}$ is independently hydrogen, halogen, alkyl, aryl, arylalkyl, arylaryl, arylheteroalkyl, heteroaryl, heteroarylalkyl $NR^{14}R^{14}$, —$C(O)R^{14}$ or —$S(O)_2R^{14}$; and each $R^{14}$ is independently hydrogen, alkyl, alkanyl, alkynyl, aryl, arylalkyl, arylheteralkyl, arylaryl, heteroaryl or heteroarylalkyl.

"Amphomycin-Type Lipopeptide Antibiotic" refers to an antibiotic characterized by a macrocyclic peptide core that includes a macrocyclic amino acid having a side chain with a primary amino group, such as a macrocyclic Dab residue, and a lipophilic fatty acid moiety. The macrocyclic peptide core includes an exocyclic amino acid, which is typically an Asn or an Asp, which intervenes the macrocycle and the fatty acid moiety. In a preferred embodiment, an amphomycin-type lipopeptide antibiotic is characterized by the following structure (I):

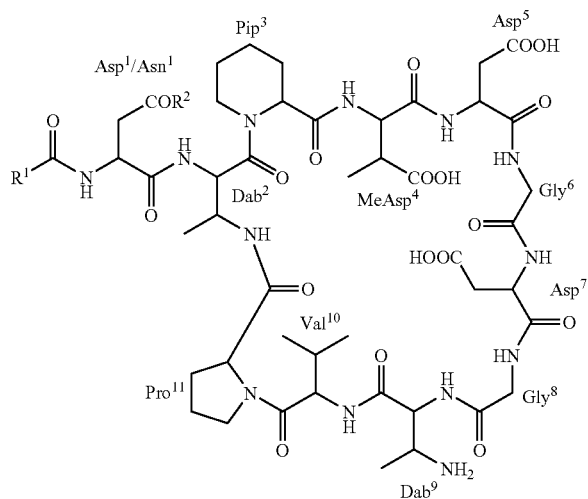

(I)

wherein:

$R^1$ is a branched or straight-chained, saturated or singly or multiply unsaturated aliphatic or hydroxy aliphatic moiety having a chain length of from 6 to 22 carbon atoms; and $R^2$ is OH or $NH_2$.

In another embodiment, the lipopeptide antibiotic has structure (I) wherein $R^1$ is selected from the group consisting of hydrogen, ($C_1$–$C_{25}$) alkyl optionally substituted with one or more of the same or different $R^{15}$ groups, ($C_1$–$C_{25}$) heteroalkyl optionally substituted with one or more of the same or different $R^{15}$ groups, ($C_5$–$C_{10}$) aryl optionally substituted with one or more of the same or different $R^{15}$ groups, ($C_5$–$C_{15}$) arylaryl optionally substituted with one or more of the same or different $R^{15}$ groups, ($C_5$–$C_{15}$) biaryl optionally substituted with one or more of the same or different $R^{15}$ groups, 5–10 membered heteroaryl optionally substituted with one or more of the same or different $R^{15}$ groups, ($C_6$–$C_{26}$) arylalkyl optionally substituted with one or more of the same or different $R^{15}$ groups and 6–26 membered heteroarylalkyl optionally substituted with one or more of the same or different $R^{15}$ groups;

each $R^{15}$ is independently selected from the group consisting of —$OR^{16}$, —$SR^{16}$, $NR^{16}R^{16}$, —CN, —$NO_2$, —$N_3$, —$C(O)OR^{16}$, —$C(O)NR^{16}R^{16}$, —$C(S)NR^{16}R^{16}$, —$C(NR^{16})NR^{16}R^{16}$, —CHO, —$R^{16}$CO, —$SO_2R^{16}$, —$SOR^{16}$, —$PO(OR^{16})_2$, —$PO(OR^{16})$, —$CO_2H$, —$SO_3H$, —$PO_3H$, halogen and trihalomethyl;

each $R^{16}$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and 6–16 membered heteroarylalkyl; and $R^2$ is OH or $NH_2$.

For convenience, amphomycin-type lipopeptide antibiotics may be abbreviated using three different conventions, illustrated below:

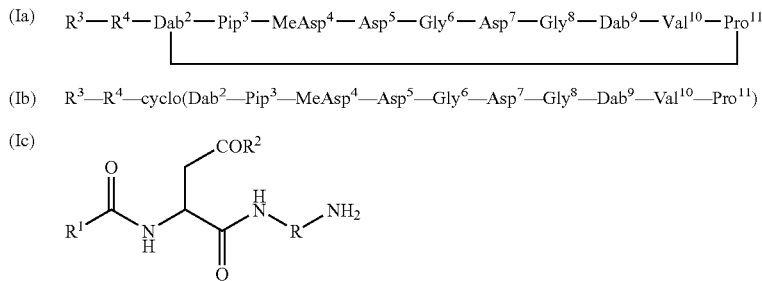

(Ia)  $R^3—R^4—Dab^2—Pip^3—MeAsp^4—Asp^5—Gly^6—Asp^7—Gly^8—Dab^9—Val^{10}—Pro^{11}$ (Ib)  $R^3—R^4—cyclo(Dab^2—Pip^3—MeAsp^4—Asp^5—Gly^6—Asp^7—Gly^8—Dab^9—Val^{10}—Pro^{11})$ (Ic)

In structures (Ia) and (Ib), $R^3$ is a branched or straight-chained, saturated or singly or multiply unsaturated fatty acid or hydroxy fatty acid having a chain length of from 6 to 22 carbon atoms and $R^4$ is an Asp or Asn residue in which the C-terminal carboxyl group is linked to the α-amino group of residue $Dab^2$ and the N-terminal amino group is linked to the carboxyl group of fatty acid $R^3$. Alternatively in structures (Ia) and (Ib), $R^4$ is an Asp or Asn residue in which the carboxy-terminal carboxyl group is linked to the α-amino group of residue $Dab^2$ and the amino-terminal amino group is either directly linked to $R^3$ (i.e., there is no amide linkage) or is linked to the carboxyl group of a fatty acid $R^3$, wherein $R^3$ is selected from the group consisting of hydrogen, ($C_1$–$C_{25}$) alkyl optionally substituted with one or more of the same or different $R^{15}$ groups, ($C_1$–$C_{25}$) heteroalkyl optionally substituted with one or more of the same or different $R^{15}$ groups, ($C_5$–$C_{10}$) aryl optionally substituted with one or more of the same or different $R^{15}$ groups, ($C_5$–$C_{15}$) arylaryl optionally substituted with one or more of the same or different $R^{15}$ groups, ($C_5$–$C_{15}$) biaryl optionally substituted with one or more of the same or different $R^{15}$ groups, 5–10 membered heteroaryl optionally substituted with one or more of the same or different $R^{15}$ groups, ($C_6$–$C_{26}$) arylalkyl optionally substituted with one or more of the same or different $R^{15}$ groups and 6–26 membered heteroarylalkyl optionally substituted with one or more of the same or different $R^{15}$ groups; each $R^{15}$ is independently selected from the group consisting of —$OR^{16}$, —$SR^{16}$, $NR^{16}R^{16}$, —CN, —$NO_2$, —$N_3$, —C(O)$OR^{16}$, —C(O)$NR^{16}R^{16}$, —C(S)$NR^{16}R^{16}$, —C($NR^{16}$)$NR^{16}R^{16}$, —CHO, —$R^{16}$CO, —$SO_2R^{16}$, —$SOR^{16}$, —PO($OR^{16}$)$_2$, —PO($OR^{16}$), —$CO_2$H, —$SO_3$H, —$PO_3$H, halogen and trihalomethyl; and each $R^{16}$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and 6–16 membered heteroarylalkyl.

In a further embodiment, N-terminal amino group of $R^4$ is attached to $R^3$ via a linker $X^1$, which may be any kind of chemical functionality that can form a covalent bond with nitrogen known to those of skill in the art. In a exemplary embodiment, $X^1$ is selected from the group consisting of —CO—, —$SO_2$—, —CS—, —PO—, —OPO—, —OC(O)—, —NHCO—, —$NR^1$CO—. In another preferable embodiment, $X^1$ is —CO—, —NHCO, or —$SO_2$. In a particularly preferred embodiment, $X^1$ is —CO—.

In structure (Ia), the "⌐" designates the linkage of the C-terminal carboxyl group of residue $Pro^{11}$ to the β-amino group of residue $Dab^2$. In structure (Ic), $R^1$ and $R^2$ are as described herein for structure (I) and R represents the peptide macrocyclic illustrated below:

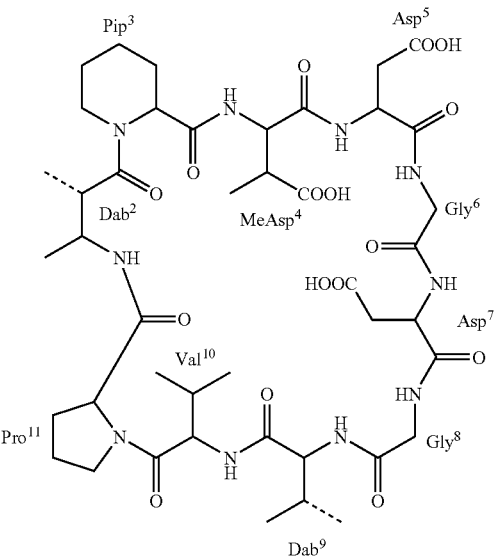

In the above macrocyclic peptide moiety, the dashed line emanating from residue $Dab^2$ indicates the point of attachment to the amide nitrogen of structure (Ic) and the dashed line emanating from residue $Dab^9$ indicates the point of attachment to the primary amino group of structure (Ic).

Skilled artisans will recognize that amphomycin-type lipopeptide antibiotics isolated from cultures typically comprise mixtures of compounds that differ with respect to the structures of their amphomycin-type macrocyclic cores (defined below) and/or their fatty acid moieties. The various different compounds comprising the mixture may be separated from one another and isolated either as sub-mixtures or as structurally pure compounds. As used herein, "amphomycin-type lipopeptide antibiotic" is intended to include the mixtures naturally produced by the producing strain, as well as any sub-mixtures and/or structurally pure compounds isolated therefrom.

Common amphomycin-type lipopeptide antibiotics include amphomycin (glumamycin) (Heinemann et al., 1953, *Antibiot. Chemother.* 3:1239–1242; Fujino et al., 1965, *Bull. Chem. Soc. Jap.* 38:515; Bodanszky et al., 1973, *J. Am. Chem. Soc.* 95:2352; Shibata et al., U.S. Pat. No. 3,160,561); aspartocin (Shay et al., U.S. Pat. No. 3,057,779; Shay et al., 1960, *Antibiotics Ann.* 194; Hausman et al., 1964, *Antimicrob. Ag. Chemother.* 352; Hausman et al., 1969, *J. Antibiotics* 22:207; Martin et al., 1960, *J. Am. Chem. Soc.* 2079); crystallomycin (Gauze et al., 1957, *Antibiotiki* 2:9–14); antibiotic A1437 (Hammann et al., EP 0 629 636 B1; Hammann et al., U.S. Pat. No. 6,194,383; Lattrell et al., U.S. Pat. No. 5,629,288); friulimycin (Vertesy et al., 2000, *J. Antibiotics* 53:816); tsushimycin (Shoji et al., 1968, *J Antibiotics* 21:439; Nishimura et al., U.S. Pat. No. 3,781,420); and zaomycin (Hinuma, 1954, *J. Antibiotics* 7(4):134–136; Kuroya, 1960, *Antibiotics Ann.* 194; Kuroya, JP 8150).

"Amphomycin-Type Macrocyclic Core" refers to the macrocycle obtained by delipidating an amphomycin-type lipopeptide antibiotic, illustrated as structural formula (II), below:

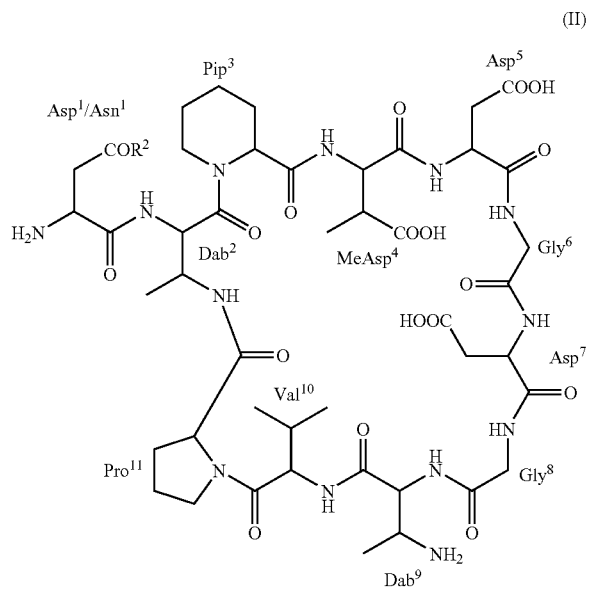

In structure (II), $R^2$ is as described herein for structure (I).

For convenience, amphomycin-type macrocyclic cores may be conveniently abbreviated using three different conventions, illustrated below:

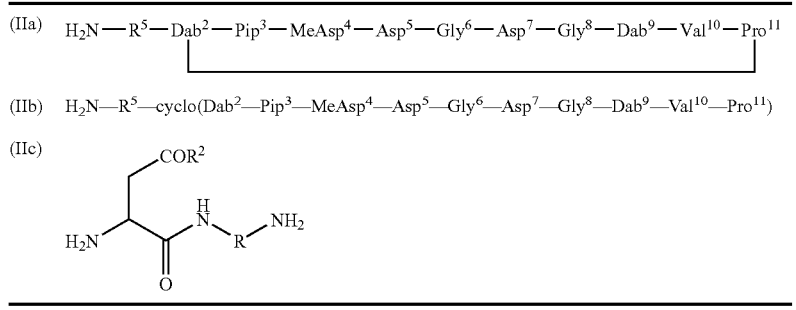

In structures (IIa) and (IIb), $H_2N—R^5$ is an Asp or Asn residue in which the C-terminal carboxyl is linked to the α-amino of residue $Dab^2$. In abbreviation (IIa), the "⌐" designates the linkage of the C-terminal carboxyl of residue $Pro^{11}$ to the β-amino of residue $Dab^2$. In structure (IIc), $R^2$ and R are as previously defined for structure (Ic).

"Structurally pure" refers to a compound composition in which a substantial percentage, e.g., on the order of 95% to 100% and preferably ranging from about 95%, 96%, 97%, 98%, 99% or more, of the individual molecules comprising the composition each contain the same number and types of atoms attached to each other in the same order and with the same bonds. As used herein, "structurally pure" is not intended to distinguish different geometric isomers or different optical isomers from one another. For example, as used herein a mixture of cis- and trans-but-2,3-ene is considered structurally pure, as is a racemic mixture. When compositions are intended to include a substantial percentage of a single geometric isomer and/or optical isomer, the nomenclature "geometrically pure" and "optically or enantiomerically pure," respectively, are used.

The phrase "structurally pure" is also not intended to discriminate between different tautomeric forms or ionization states of a molecule, or other forms of a molecule that result as a consequence of equilibrium phenomena or other reversible interconversions. Thus, a composition of, for example, an organic acid is structurally pure even though some of the carboxyl groups may be in a protonated state (—COOH) and others may be in a deprotonated state (—COO$^-$). Likewise, a composition comprising a mixture of keto and enol tantomers, unless specifically noted otherwise, is considered structurally pure.

The $Dab^9$ Derivatives

The compounds of the invention are derivatives of amphomycin-type lipopeptide antibiotics that are substituted at the β-amino group of the macrocyclic $Dab^9$ residue with a substituent that includes a primary or secondary amine. In one illustrative embodiment, the compounds of the invention are amphomycin-type lipopeptide antibiotic derivatives according to structural formula (III):

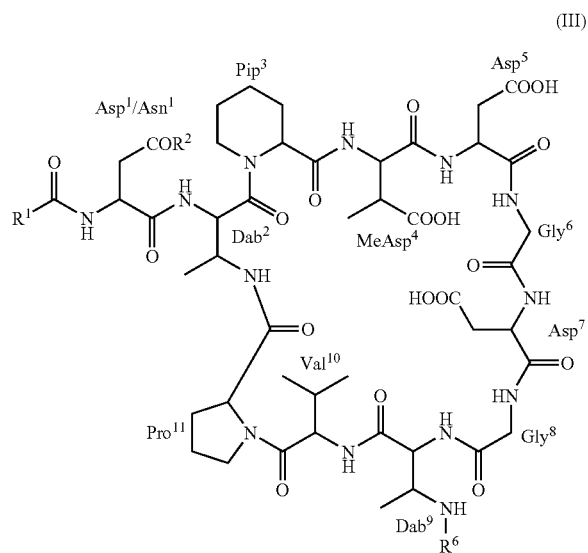

(III)

including the salts thereof, wherein:

$R^1$ and $R^2$ are as previously defined for structure (I); and $R^6$ is (i) at least one amino acid, (ii) a substituent including a primary or secondary amine, or (iii) selected from the group consisting of hydrogen, $(C_1–C_{25})$ alkyl optionally substituted with one or more of the same or different $R^{15}$ groups, $(C_1–C_{25})$ heteroalkyl optionally substituted with one or more of the same or different $R^{15}$ groups, $(C_5–C_{10})$ aryl optionally substituted with one or more of the same or different $R^{15}$ groups, $(C_5–C_{15})$ arylaryl optionally substituted with one or more of the same or different $R^{15}$ groups, $(C_5–C_{15})$ biaryl optionally substituted with one or more of the same or different $R^{15}$ groups, 5–10 membered heteroaryl optionally substituted with one or more of the same or different $R^{15}$ groups, $(C_6–C_{26})$ arylalkyl optionally substituted with one or more of the same or different $R^{15}$ groups and 6–26 membered heteroarylalkyl optionally substituted with one or more of the same or different $R^{15}$ groups;

each $R^{15}$ is independently selected from the group consisting of —$OR^{16}$, —$SR^{16}$, $NR^{16}R^{16}$, —CN, —$NO_2$, —$N_3$, —$C(O)OR^{16}$, —$C(O)NR^{16}R^{16}$, —$C(S)NR^{16}R^{16}$, —$C(NR^{16})NR^{16}R^{16}$, —CHO, —$R^{16}CO$, —$SO_2R^{16}$, —$SOR^{16}$, —$PO(OR^{16})_2$, —$PO(OR^{16})$, —$CO_2H$, —$SO_3H$, —$PO_3H$, halogen and trihalomethyl; and each $R^{16}$ is independently selected from the group consisting of hydrogen, $(C_1–C_6)$ alkyl, $(C_5–C_{10})$ aryl, 5–10 membered heteroaryl, $(C_6–C_{16})$ arylalkyl and 6–16 membered heteroarylalkyl.

For convenience of discussion, the compounds of structure (III) may be abbreviated as illustrated in structures (IIIa–c), below:

(IIIa)

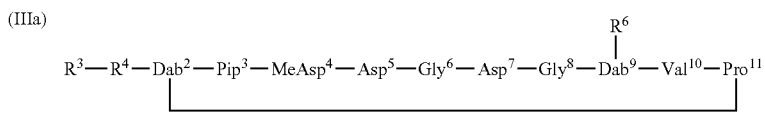

(IIIb)

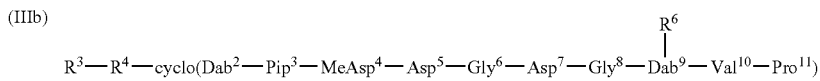

(IIIc)

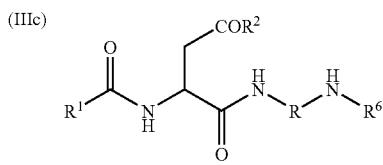

In structures (IIIa) and (IIIb), $R^3$ and $R^4$ are as described herein for structure (Ia) and $R^6$ is as described herein for structure (III). In structure (IIIc), $R^1$ and $R^2$ are as described herein for structure (I) and $R^6$ is as described herein for structure (III). In structures (IIIa) and (IIIb), the $R^6$ substituent is linked to the β-amino group of the illustrated $Dab^9$ residue (see, e.g., structure III).

In some embodiments, the compounds of the invention are $Dab^9$ derivatives of parent amphomycin-type lipopeptide antibiotics produced from cultures. Examples of such parent amphomycin-type lipopeptide antibiotics include, but are not limited to, amphomycin (glumamycin), aspartocin, crystallomycin, friulimycin, tsushimycin and zaomycin. Skilled artisans will recognize that in these embodiments, the structures of residue $R^4$ and/or fatty acid moiety $R^3$ in formulae (Ia) and (Ib) will be dictated in large part by the producing strain and culture conditions. Skilled artisans will also recognize that in these embodiments, the parent amphomycin-type lipopeptide antibiotics may comprise mixtures of compounds that differ from one another with respect to the structure of residue $R^4$ and/or fatty acid moiety $R^3$. As will be discussed in more detail below in connection with the synthesis of the compounds of the invention, the desired compounds of the invention may be obtained by appropriate selection of the parent amphomycin-type lipopeptide antibiotic used as a starting material. For example, although preparations of aspartocin, amphomycin, zaomycin and tsushimycin isolated from cultures comprise mixtures of compounds, they are all believed to share the same amphomycin-type macrocyclic core: the amphomycin-type macrocyclic core of structural formula (II) in which $R^2$ is OH. Likewise, in preparations of friulimycin, the components of the mixture are all believed to share the same amphomycin-type macrocyclic core: the amphomycin-type macrocyclic core of structural formula (II) in which $R^2$ is $NH_2$. Thus, it is believed that the compounds comprising these respective antibiotic mixtures differ from one another only with respect to the structures of their fatty acid moieties. Alternatively, antibiotic A1437 comprises a mixture of compounds that are believed to differ from one another with respect to the structures of their amphomycin-type macrocyclic cores and fatty acid moieties (see, eg., U.S. Pat. No. 6,194,383).

All of these various parent amphomycin-type lipopeptide antibiotics may be used as starting materials to produce the desired $Dab^9$ derivatives of the invention. Structurally pure $Dab^9$ derivatives of the invention may be obtained by separating and isolating the component compounds of the parent amphomycin-type lipopeptide antibiotic starting material prior to derivatization of the macrocyclic $Dab^9$ residue, or, alternatively, separating the component compounds of the resultant mixture following derivatization, as will be described in more detail, below.

Moreover, in many instances, the exact structures of the fatty acid moieties of such parent amphomycin-type lipopeptide antibiotics are unknown. Compounds of the invention having a fatty acid moiety of a specified structure may be obtained by delipidating the parent amphomycin-type lipopeptide antibiotic starting materials and reacting the delipidated intermediate with a fatty acid or other substituent (e.g., a lipophilic fragment) of specified structure. The resultant product may then be derivatized at the $Dab^9$ residue to yield a $Dab^9$ derivative of the invention. Alternatively, a $Dab^9$ derivative of the invention prepared by derivatizing a parent amphomycin-type lipopeptide antibiotic may be delipidated and the $Dab^9$ derivatized delipidated intermediate reacted with a fatty acid or other substituent of specified structure.

Fatty acids suitable for use in producing an appropriate fatty acid moiety $R^3$ are well known to skilled artisans (see, e.g., Römpp Chemie Lexicon, Prof. Falbe and Prof. Regitz, 9$^{th}$ Edition, Georg Thieme Verlag Stuttgart, New York; and Hawley, 3$^{rd}$ Edition, Van Nostrand Reinhold Company, New York, each of which is incorporated herein by reference).

In one embodiment, a fatty acid is selected that yields a compound of the invention having a fatty acid moiety $R^3$ that is identical to a fatty acid moiety of a known amphomycin-type lipopeptide antibiotic. Such fatty acids are well known to those of skill in the art. Non-limiting illustrative examples are provided in, e.g., U.S. Pat. No. 6,194,383 (see especially Cols. 5–8), which is incorporated herein by reference.

However, the fatty acid need not correspond to a fatty acid of a known amphomycin-type lipopeptide antibiotic. Suitable fatty acids include, by way of example and not limitation, the various fatty acids, such as fatty acids that are unbranched and saturated (e.g., caproic, enanthic, caprylic, pelargonic, capric, undecanoic, lauric, tridecanoic, myristic, pentadecanoic, palmitic, margaric, stearic, nonadecanoic, arachidic, behenic, lignoceric, pentacosenoic, and the like); branched and saturated (e.g., isobutyric, isovaleric, isopalmitic and the like, and corresponding acids in the ante-iso configuration and may contain methoxy or hydroxy substitutions); monoenoic (e.g., obtusilic, caproleic, lauroleic, linderic, myristoleic, physeteric, tsuzuic, palmitoleic, petroselinic, oleic, vaccenic, gadoleic, gondoic, cetoleic, erucic, nervonic, and the like); polyenoic (e.g., linoleic, γ-linoleic, arachidonic, stearidonic, and the like, and methylene interrupted polyenes, polymethylene interrupted polyenes, conjugated fatty acids, and halogenated fatty acids). See also U.S. Pat. No. 6,194,383, which is incorporated herein by reference.

Typically, the fatty acid is a fatty acid or hydroxy fatty acid with a chain length of from 6–22 carbon atoms and usually from 10–20 carbon atoms. The fatty acid or hydroxy fatty acid may be branched or linear, saturated or singly or multiply unsaturated, or combinations thereof. In one embodiment, the fatty acid is a saturated or singly unsaturated fatty acid comprising 11, 12, 13, 14 or 15 carbon atoms that is either linear or singly branched, preferably in the iso or ante-iso configuration. In another embodiment, the fatty acid is a saturated or singly unsaturated hydroxy fatty acid comprising 11, 12, 13, 14 or 15 carbon atoms that is either linear or singly branched, preferably in the iso or ante-iso configuration. In a specific embodiment, the hydroxy fatty acid is hydroxylated at position 2, 3 and/or at the end of the chain.

Alternatively $R^3$ may be directly linked to the N-terminal amino group of the $R^4$ Asp or Asn residue (see, e.g., structures IIIa and IIIb), wherein $R^3$ is selected from the group consisting of hydrogen, $(C_1–C_{25})$ alkyl optionally substituted with one or more of the same or different $R^{15}$ groups, $(C_1–C_{25})$ heteroalkyl optionally substituted with one or more of the same or different $R^{15}$ groups, $(C_5–C_{10})$ aryl optionally substituted with one or more of the same or different $R^{15}$ groups, ($C_5$–$C_{15}$) arylaryl optionally substituted with one or more of the same or different $R^{15}$ groups, ($C_5$–$C_{15}$) biaryl optionally substituted with one or more of the same or different $R^{15}$ groups, 5–10 membered heteroaryl optionally substituted with one or more of the same or different $R^{15}$ groups, ($C_6$–$C_{26}$) arylalkyl optionally substituted with one or more of the same or different $R^{15}$ groups and 6–26 membered heteroarylalkyl optionally substituted with one or more of the same or different $R^{15}$ groups; each $R^{15}$ is independently selected from the group consisting of —$OR^{16}$, —$SR^{16}$, $NR^{16}R^{16}$, —CN, —$NO_2$, —$N_3$, —C(O)$OR^{16}$, —C(O)$NR^{16}R^{16}$, —C(S)$NR^{16}R^{16}$, —C($NR^{16}$)$NR^{16}R^{16}$, —CHO, —$R^{16}$CO, —$SO_2R^{16}$, —$SOR^{16}$, —PO($OR^{16}$)$_2$, —PO($OR^{16}$), —$CO_2$H, —$SO_3$H, —$PO_3$H, halogen and trihalomethyl; and each $R^{16}$ is independently selected from the group consisting of hydrogen, ($C_1$–$C_6$) alkyl, ($C_5$–$C_{10}$) aryl, 5–10 membered heteroaryl, ($C_6$–$C_{16}$) arylalkyl and 6–16 membered heteroarylalkyl In the compounds of structures (IIIa) and (IIIb), $R^4$ represents an Asp residue or an Asn residue. Whether $R^4$ is Asp or Asn will depend upon the choice of parent amphomycin-type lipopeptide antibiotic used as a starting material in the synthesis of the $Dab^9$ derivatives of the invention, as will be apparent to those of skill in the art. For example, $Dab^9$ derivatives in which $R^4$ is Asp may be prepared from amphomycin, aspartocin, tsushimycin, and/or the Asp fraction of antibiotic A1437. $Dab^9$ derivatives of the invention in which $R^4$ is Asn may be prepared from friulimycin and/or from the Asn fraction of antiobiotic A1437. The Asp and Asn fractions of antibiotic A1437 may be isolated from a preparation of cultured antibiotic A1437 according to the methods described in, for example, U.S. Pat. No. 6,194,383, which are incorporated herein by reference. $Dab^9$ derivatives of the invention that comprise a mixture of compounds, some of which are compounds according to structural formulae (IIIa) or (IIIb) in which $R^4$ is Asp and others of which are compounds according to structural formulae (IIIa) or (IIIb) in which $R^4$ is Asn, may be prepared from antibiotic A1437.

In the $Dab^9$ derivatives of structural formulae (III), (IIIa), (IIIb) and (IIIc), $R^6$ may be a substituent that includes a primary or secondary amine group. In one preferred embodiment, the primary or secondary amine group has the formula —$NHR^7$, where $R^7$ is hydrogen or ($C_1$–$C_4$) alkyl. In another preferred embodiment, the primary or secondary amine group may be spaced away from the macrocyclic $Dab^9$ residue via an optional linking moiety, as described herein. The present invention is based, in part, on the surprising discovery that amphomycin-type lipopeptide antibiotics derivatized at the macrocyclic $Dab^9$ residue with an $R^6$ substituent retain substantially the same antimicrobial properties of the parent amphomycin-type lipopeptide antibiotics from which they are derived, but have altered solubility properties, which may lead to the $Dab^9$ derivatives having improved therapeutic properties or spectra as compared to the parent amphomycin-type lipopeptide antibiotics from which they are derived.

As mentioned above, the primary or secondary amine —$NHR^7$ is spaced away from the β-nitrogen of the $Dab^9$ residue ("$Dab^9$ β-nitrogen") via an optional linking moiety.

Referring to FIG. 1, which illustrates a representative $Dab^9$ derivative of the invention in which $R^1$ and $R^2$ are as defined for structural formula (III) and $R^7$ is as defined above, the linking moiety 1 comprises a linkage group 2, which is attached to the $Dab^9$ β-nitrogen 3, and an optional spacer 4. In one embodiment, the linkage group 2 and spacer 4 taken together comprise a sufficient number of atoms such that the distance between the $Dab^9$ β-nitrogen 3 and the nitrogen atom of the amine group —$NHR^7$ ("amine nitrogen") 5 is in the range of about 1 Å to about 10 Å. Typically, the linkage group 2 is a moiety that, when taken together with the $Dab^9$ β-nitrogen atom 3 to which it is bonded, yields a linkage 6 that is stable to the physiologic conditions under which the compounds of the invention will be used. Non-limiting examples of suitable linkages 6 include amide, imide, sulfonamide, sulfonimide, amidine, carbonate, carbamate, thiourea, urea, and the like. Accordingly, non-limiting examples of suitable linking groups 2 include —C(O)—, —S(O)$_2$—, —C(NH)— and —C(O)O— groups.

The spacer 4, which may be present or absent, may include virtually any combination of carbon and/or heteroatoms suitable for spacing, when necessary, the primary or secondary amine group away from the linkage formed between the linking group and the $Dab^9$ β-nitrogen. Suitable groups which may comprise the spacer 4 include, but are not limited to, —$CH_2$—, —CH=CH—, —C≡C—, —O—, —S—, —NH—, —NH—NH—, —N=N—, —C(O)—, —S(O)$_2$—, —S(O)$_2$—O— and —C(NH)— groups. These and other groups that will be apparent to those of skill in the art may be used in a multitude of combinations to create suitable spacers 4. Skilled artisans will recognize that the exact number of atoms necessary to achieve a particularly desired spacing will depend upon, among other things, the types of atoms (e.g., N, O, C, etc.) and bonds (e.g., single, double, triple, etc.) comprising the linking moiety 1 and will be able to select combinations of groups yielding an appropriate spacing.

One or more of the atoms comprising the spacer 4 may be further substituted with a substituent. The substituent may be virtually any group that can be attached to the type of atom being substituted. In one embodiment, such substituents, which may be the same or different, are selected from the group consisting of —$NR^8R^8$, —$OR^8$, —$SR^8$, halogen, trihalomethyl, —CN, —C(O)$R^8$, —C(O)$OR^8$, —C(O)$NR^8R^8$, amidine, guanidine, alkyl optionally substituted with one or more of the same or different $R^9$, aryl optionally substituted with one or more of the same or different $R^9$, arylalkyl optionally substituted with one or more of the same or different $R^9$, heteroalkyl optionally substituted with one or more of the same or different $R^9$, heteroarylalkyl optionally substituted with one or more of the same or different $R^9$, wherein each $R^8$ is independently selected from the group consisting of hydrogen, alkyl, aryl, arylalkyl, heteroaryl and heteroarylalkyl, and each $R^9$ is independently selected from the group consisting of —$NR^8R^8$, —$OR^8$, —$SR^8$, halogen, trihalomethyl, —CN, —C(O)$R^8$, —C(O)$OR^8$, —C(O)$NR^8R^8$, amidine, guanidine, alkyl, aryl, arylalkyl, heteroaryl, and heteroarylalkyl.

In one embodiment of the invention, the spacer 4 is a ($C_1$–$C_6$) branched or unbranched alkyldiyl, which optionally includes one or more, typically one, of the same or different previously described substituent groups. Preferred alkyldiyls are substituted or unsubstituted alkylenos. Especially preferred alkyldiyls are substituted or unsubstituted $(C_1-C_4)$ alkanos.

Thus, in one illustrative embodiment of the $Dab^9$ derivatives according to structural formulae (III), (IIIa), (IIIb) and (IIIc), amine-containing substituent $R^6$ has the structural formula (IV):

$$-X-R^{10}-NHR^7 \qquad (IV)$$

wherein:
$R^7$ is as previously defined;
$R^{10}$ is $(C_1-C_4)$ alkano; and
$X$ is $-C(O)-$, $-C(NH)-$ or $-S(O)_2-$.

In another illustrative embodiment of the $Dab^9$ derivatives of structural formulae (III), (IIIa), (IIIb) and (IIIc), amine-containing substituent $R^6$ has the structural formula (V):

$$-X-(R^{11}R^{11})_n-NHR^7 \qquad (V)$$

wherein:
n is an integer from 1 to 6;
each $R^{11}$ is independently selected from the group consisting of hydrogen, amino, amido, amidino, carboxy, guanidino, hydroxy, sulfanyl, $(C_1-C_4)$ alkyl, $(C_1-C_4)$ alkyl substituted with one or more of the same or different $R^{12}$, $(C_5-C_{10})$ aryl, $(C_5-C_{10})$ aryl substituted with one or more of the same or different $R^{12}$, $(C_6-C_{13})$ arylalkyl, $(C_6-C_{13})$ arylalkyl substituted with one or more of the same or different $R^{12}$, 5–10 membered heteroaryl, 5–10 membered heteroaryl substituted with one or more of the same or different $R^{12}$, 6–13 membered heteroarylalkyl and 6–13 membered heteroarylalkyl substituted with one or more of the same or different $R^{12}$;
each $R^{12}$ is independently selected from the group consisting of amino, amido, amidino, carboxyl, guanidino, hydroxy and sulfanyl; and
X and $R^7$ are as previously defined for structure (IV).

In a specific embodiment of structural formula (V), n is 1, 2 or 3 and/or only one $R^{11}$ is other than hydrogen.

In another embodiment, the $Dab^9$ derivatives of structural formulae (IIa) and (IIIb), substituent $R^6$ has the structural formula (VI) as follows:

$$-X^1-R^3 \qquad (VI)$$

wherein:
$X^1$ is a linker, which may be any kind of chemical functionality that can form a covalent bond with nitrogen known to those of skill in the art. In a exemplary embodiment, $X^1$ is selected from the group consisting of $-CO-$, $-SO_2$, $-CS-$, $-PO-$, $-OPO-$, $-OC(O)-$, $-NHCO-$, $-NR^1CO-$. In another preferable embodiment, $X^1$ is $-CO-$, $-NHCO-$, or $-SO_2$. In a particularly preferred embodiment, $X^1$ is $-CO-$.

$R^3$ is selected from the group consisting of hydrogen, $(C_1-C_{25})$ alkyl optionally substituted with one or more of the same or different $R^{15}$ groups, $(C_1-C_{25})$ heteroalkyl optionally substituted with one or more of the same or different $R^{15}$ groups, $(C_5-C_{10})$ aryl optionally substituted with one or more of the same or different $R^{15}$ groups, $(C_5-C_{15})$ arylaryl optionally substituted with one or more of the same or different $R^{15}$ groups, $(C_5-C_{15})$ biaryl optionally substituted with one or more of the same or different $R^{15}$ groups, 5–10 membered heteroaryl optionally substituted with one or more of the same or different $R^{15}$ groups, $(C_6-C_{26})$ arylalkyl optionally substituted with one or more of the same or different $R^{15}$ groups and 6–26 membered heteroarylalkyl optionally substituted with one or more of the same or different $R^{15}$ groups;

each $R^{15}$ is independently selected from the group consisting of $-OR^{16}$, $-SR^{16}$, $NR^{16}R^{16}$, $-CN$, $-NO_2$, $-N_3$, $-C(O)OR^{16}$, $-C(O)NR^{16}R^{16}$, $-C(S)NR^{16}R^{16}$, $-C(NR^{16})NR^{16}R^{16}$, $-CHO$, $-R^{16}CO$, $-SO_2R^{16}$, $-SOR^{16}$, $-PO(OR^{16})_2$, $-PO(OR^{16})$, $-CO_2H$, $-SO_3H$, $-PO_3H$, halogen and trihalomethyl; and each $R^{16}$ is independently selected from the group consisting of hydrogen, $(C_1-C_6)$ alkyl, $(C_5-C_{10})$ aryl, 5–10 membered heteroaryl, $(C_6-C_{16})$ arylalkyl and 6–16 membered heteroarylalkyl.

The linker $X^1$ may further comprise a spacer moiety that is hydrophilic or hydrophobic, long or short, rigid, semirigid or flexible. A wide variety of spacers comprised of stable bonds suitable for spacing, for example amine $R^6$ substituent groups, from the $Dab^9$ β-amino group, are known in the art, and include by way of example and not limitation, alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, spacers may include single, double, triple or aromatic carbon-carbon bonds, nitrogen-nitrogen bonds, carbon-nitrogen, carbon-oxygen bonds and/or carbon-sulfur bonds, and may therefor include functionalities such as carbonyls, ethers, thioethers, carboxamides, sulfonamides, ureas, urethanes, hydrazines, and the like.

Choosing a suitable linker and/or spacer is within the capabilities of those having skill in the art. For example, where a rigid linker or spacer is desired, it may be a rigid polyunsaturated alkyl or an aryl, biaryl, heteroaryl, and the like. Where a flexible linker or spacer is desired, it may be a flexible peptide such as Gly-Gly-Gly or a flexible saturated alkanyl or heteroalkanyl. Hydrophilic linkers or spacers may be, for example, polyalcohols or polyethers such as polyalkyleneglycols. Hydrophobic linkers or spacers may be, for example, alkyls or aryls.

In a preferred embodiment of the $Dab^9$ derivatives of structural formulae (III), (IIIa), (IIIb) and (IIIc), substituent $R^6$ is an amino acid which is linked via its terminal carboxyl group to the β-amino group of the macrocyclic $Dab^9$ residue to form an amide linkage. Such amino acids may include, by way of example and not limitation, α-, β- and γ-amino acids. The amino acids may optionally include side chain moieties, such as a side chain moiety of one of the twenty genetically encoded amino acids, or a common analog thereof. Any chiral centers in the amino acid may be in either the R- or S-configuration. Non-limiting examples of suitable amino acids include the twenty genetically encoded amino acids; the various amino acids listed in Fasman, *CRC Practical Handbook at Biochemistry and Molecular Biology*, 1989, CRC Press, Inc., Boca Raton, Fla. at pp. 4–60, the disclosure of which is incorporated herein by reference, and the α, β-unsaturated amino acids listed in Fasman, 1989, supra, at pp. 69, the disclosure of which is incorporated herein by reference. Other suitable amino acids will be apparent to those of skill in the art.

Methods of Synthesis

The compounds of the invention may be synthesized via several different synthetic routes using commercially available starting materials and/or starting materials prepared by conventional synthetic and/or biosynthetic methods. Two general synthetic approaches are illustrated in Scheme (I), below:

In Scheme (I), $R^1$ and $R^2$ are as previously defined in structural formula (IIIc). According to Scheme (I), a parent amphomycin-type lipopeptide antibiotic 10 is acylated with an appropriately protected reactant 12, which in the specific illustrated example is Fmoc-protected glycine, to yield protected intermediate 14. Reaction conditions for coupling primary amines such as antibiotic 10 with carboxylic acids such as reactant 12 to yield amide linkages are known to those of skill in the art and may be found in any compendium of standard synthetic methods and/or literature related to the

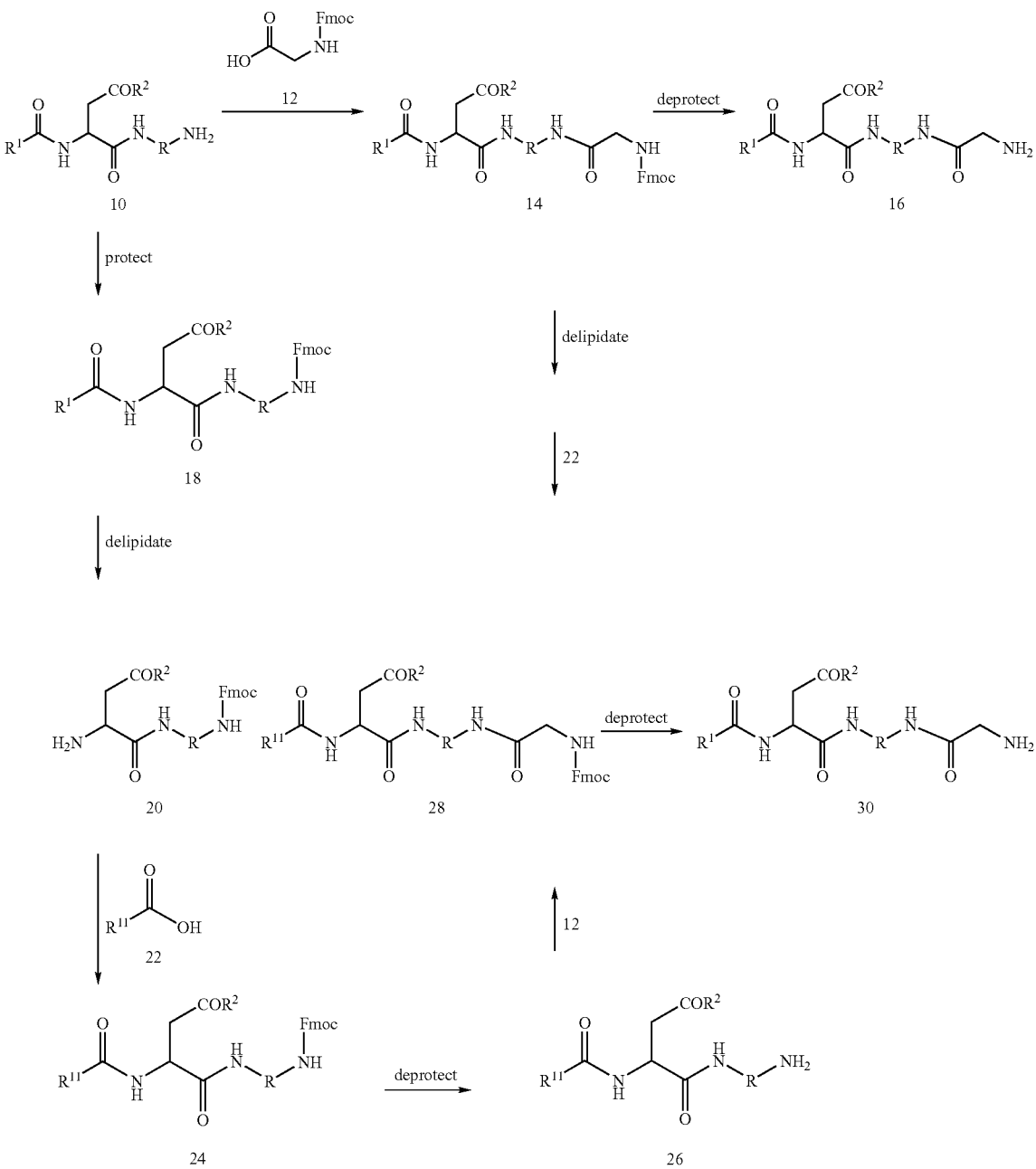

Scheme (I)

synthesis of peptides and proteins. See e.g., March, J., *Advanced Organic Chemistry; Reactions, Mechanisms and Structure*, 4th ed., 1992; Larock, *Comprehensive Organic Transformations*, VCH, New York, 1999; Bodanzsky, *Principles of Peptide Synthesis*, Springer Verlag, 1984; Bodanzsky, *Practice of Peptide Synthesis*, Springer Verlag, 1984; Lloyd-Williams et al., *Chemical Approaches to the Synthesis of Peptides and Proteins*, CRC Press, 1997 (see especially pp. 105–114); and Atherton & Sheppard, *Solid Phase Peptide Synthesis. A Practical Approach*, IRL Press, 1989, each of which is incorporated herein by reference). Specific conditions are provided in the Examples section, infra.

Protected intermediate 14 is then deprotected to yield Dab$^9$ derivative 16. While the method is illustrated using an Fmoc protecting group, skilled artisans will recognize that other protecting groups may be employed. Moreover, in some instances, reactant 12 may include other and/or additional functionalities that may require protection. Groups suitable for protecting a wide variety of different functionalities, as well as conditions for their removal, are well known and will be apparent to those of skill in the art. Specific guidance for selectively protecting a wide variety of functionalities may be found, for example, in Greene & Wuts, *Protective Groups in Organic Synthesis*, 3$^{rd}$ edition, 1999 ("Greene & Wuts"), which is incorporated herein by reference. Preferred protecting groups are those that may be easily removed. Preferred groups for protecting primary amines are tert-butyloxycarbonyl ("t-Boc"), 9-fluorenyl-methoxycarbonyl ("Fmoc") and benzyloxycarbonyl ("Z").

Parent amphomycin-type lipopeptide antibiotic 10 may be obtained by isolation from a culture of a microorganism known to produce the antibiotic. Microorganisms for producing amphomycin-type lipopeptide antibiotics are well-known, as are conditions for isolating, and optionally further purifying, the resultant antibiotics. For example, strains for producing amphomycin (glumamycin) include *Streptomyces canus* (ATCC #12237; see also *Heinemann* et al., 1953, *Antibiot. Chemother.* 3:1239–1242) and *Streptomyces zaomyceticus* (ATCC #13876; see also U.S. Pat. No. 3,160,561 to Shibata et al.). Strains for producing aspartocin include *Streptomyces griseus* subspecies *sprialis* (ATCC #13733; see also U.S. Pat. No. 3,057,779 to Shay et al.) and *Streptomyces violaceus* (Rossi-Doria) Waksman (ATCC #13734; see also U.S. Pat. No. 3,057,779). Strains for producing crystallomycin include *Streptomyces violaceoniger* var. *crystallomycini* (Gauze et al., 1957, Antibiotiki 2(6):9–14). Strains for producing antibiotic A1437 include *Actinoplanes* sp. (DSM #7358; see also U.S. Pat. No. 6,194,383 to Hammann et al.) Strains for producing friulimycin include *Actinoplanes friuliensis* (HAG #010964). Strains for producing tsushimycin include *Streptomyces pseudogriseolus* Okami and Umezawa (ATCC pseudogriseolus #21139 and #21140; see also U.S. Pat. No. 3,781,420 to Nishimura et al.) and *Streptomyces pseudogriseolus* subspecies *glucofermentans* Nishimura and Otsuka (ATCC #21141; see also U.S. Pat. No. 3,781,420 to Nishimura et al.). Strains for producing zaomycin include *Streptomyces zaomyceticus* Hinuma (NRRL #B-2038). Conditions for culturing and isolating the various lipopeptide antibiotics are found in the above-cited patents and references, as well as the various references mentioned previously in connection with these various antibiotics, the disclosures of which are incorporated herein by reference.

As discussed previously, in most instances, amphomycin-type lipopeptide antibiotics 10 isolated from cultures are mixtures of compounds that differ with respect to the structures of $R^1$ and/or $R^2$. For example, amphomycin is a mixture of compounds 10 in which $R^2$ is OH and the fatty acid moiety $R^1$—C(O)— is a mixture of iso and ante-iso $C_{12}$ and $C_{13}$ fatty acids. Aspartocin is a mixture of compounds 10 in which $R^2$ is OH and the fatty acid moiety $R^1$—C(O)— is a mixture of iso and ante-iso $C_{13}$ and $C_{14}$ fatty acids. Tsushimycin is a mixture of compounds 10 in which $R^2$ is OH and the fatty acid moiety $R^1$—C(O)— is a mixture of iso and ante-iso $C_{14}$ and $C_{15}$ fatty acids. Friulimycin is a mixture of compounds 10 in which $R^2$ is $NH_2$ and the fatty acid moiety $R^1$—C(O)— is a mixture of iso and ante-iso $C_{13}$ and $C_{15}$ fatty acids. Antibiotic A1437 is a complex mixture of 11 compounds, some of which $R^2$ is OH and in others of which $R^2$ is $NH_2$ and the fatty acid moiety is a mixture of iso and ante-iso $C_{13}$, $C_{14}$ and $C_{15}$ fatty acids. In many instances, culture conditions useful for producing one or more of the compounds of the mixtures in greater or lesser yields are known (see, e.g., *J. Biotechnology* 7:283–292, 1988). Such methods may be used in conjunction with the invention to provide mixtures of Dab$^9$ derivatives having fatty acid moieties of defined molar ratios.

Amphomycin-type lipopeptide antibiotics 10 isolated from cultures may be used directly in Scheme (I) without prior separation and isolation of the various components of the mixtures, or they may be first separated, either with respect to the fatty acids and/or, in the case of antibiotic A1437, with respect to $R^2$, into structurally pure compounds or sub-fractions or sub-mixtures. Methods for separating individual components or sub-mixtures of antibiotic preparations are well-known and will be apparent to those of skill in the art. Specific suitable methods are provided, for example, in U.S. Pat. No. 6,194,383 (see especially Cols. 10–12), which is incorporated herein by reference, and in the Examples section, infra.

In many instances, the structures of the fatty acid moieties of amphomycin-type lipopeptide antibiotics 10 may be unknown. In instances where Dab$^9$ derivatives of the invention having specified fatty acid moieties are desired, or where it is desirable for the Dab$^9$ derivative to be structurally pure, geometrically pure or optically pure, with respect to the fatty acid moiety, rather than isolating components of a cultured antibiotic preparation, it may be more convenient or desirable to replace the natural fatty acid moiety of the cultured antibiotic 10 with a synthetic fatty acid moiety of specified structure. As illustrated in Scheme (I), this may be achieved by several synthetic strategies.

According to a first strategy, amphomycin-type lipopeptide antibiotic 10 is first protected at the β-amino group of the macrocyclic Dab$^9$ residue to yield protected intermediate 18. Again, while the illustrated protecting group is Fmoc, skilled artisans will appreciate that other commonly-known amine protecting groups may be used. Protected intermediate 18 is then delipidated to yield protected amphomycin-type macrocyclic core 20. Protected core 20 is then acylated with fatty acid 22, again using standard chemistries, to yield protected amphomycin-type lipopeptide antibiotic 24. In fatty acid 22, $R^{11}$ represents the aliphatic chain of the fatty acid, and may be any of the aliphatic or hydroxy aliphatic chains previously described for $R^1$ of structure (III).

Protected antibiotic 24 is the deprotected to yield compound 26, reacted with reagent 12 to yield protected $Dab^9$ derivative 28 which, following deprotection, yields $Dab^9$ derivative 30. When parent amphomycin-type lipopeptide antibiotic 10 is a mixture of compounds that all share the same amphomycin-type macrocyclic core, such as amphomycin, aspartocin, friulimycin, tsushimycin or zaomycin, this method may be used to synthesize $Dab^9$ derivatives of the invention that are structurally pure without having to isolate the various fatty acid fractions of the parent amphomycin-type lipopeptide antibiotic 10 from one another. Delipidation yields a mixture comprising the various fatty acids and the protected amphomycin-type macrocyclic core. The protected macrocyclic core may be readily isolated in high purity from this mixture using any art-known technique, such as high performance liquid chromatography, counter current extraction, centrifugation, filtration, precipitation, ion exchange chromatography, gel electrophoresis, affinity chromatography, etc. Specific procedures that may be used directly or that may be routinely adapted to isolate a particular protected macrocyclic core are described in Debono et. al., 1988, *J. Antibiotics* 41:1093 and U.S. Pat. No. 5,039,789 (see, e.g., Cols. 30–34), each of which is incorporated herein by reference. Additional chemistries and procedures that may be used directly to delipidate and relipidate parent amphomycin-type lipopeptide antibiotic 10 are found in U.S. Pat. No. 5,629,288 to Lattrell et al., the disclosure of which is incorporated herein by reference.

In an alternative route, protected $Dab^9$ derivative 14 is delipidated and acylated with fatty acid 22, yielding protected $Dab^9$ derivative 28 which, following deprotection, yields $Dab^9$ derivative 30. This alternative route is advantageous in that it does not require separate protection of the macrocyclic $Dab^9$ β-amino group.

Generally, the fatty acid moiety of protected amphomycin-type lipopeptide antibiotic 18 and/or protected $Dab^9$ derivative 14 may be cleaved with an enzyme. The enzyme may be, for example, a degradative enzyme such as a peptidase, esterase or thiolase, of which numerous examples exist in the art. Preferably, the enzyme is a deacylase.

In an exemplary embodiment, the cleavage step involves culturing a microorganism that produces a deacylase in an appropriate culture medium and contacting protected $Dab^9$ derivative 14 or protected antibiotic 18 with the culture medium containing the deacylase. Microorganisms that produce deacylases are well known to those of skill in the art. In a preferred embodiment, the microorganism *Actinoplanes utahensis* (NRRL #12052) produces a suitable deacylase.

Growing inocula, inoculating media, culturing media and conditions for culturing such enzymes are also well known to those of skill in the art and exemplary methods for *Actinoplanes utahensis* (NRRL #12052) are described in Boeck et al., 1988, *J. Antibiot.* 41:1085; Debono et. al., 1988, *J. Antibiotics* 41:1093; U.S. Pat. No. 4,524,135 (see, e.g., Cols. 22–23) and U.S. Pat. No. 5,039,789 (see, e.g., Col. 29, lines 9–63); each of which is incorporated herein by reference.

In one embodiment, compounds 14 or 18 are delipidated by contacting them with a culture medium comprising *Actinoplanes utahensis* (NRRL #12052) for about 4 to 16 hours at a temperature of about 29° C. The reaction may be monitored by chromatography or other routine techniques, thereby permitting shorter or longer incubations, as needed. Additional methods which may be used to delipidate compounds 14 and/or 18 are found in Debono et. al., 1988, *J. Antibiotics* 41:1093; U.S. Pat. No. 5,039,789 (see, e.g., Cols. 29–34) and U.S. Pat. No. 5,629,288, each of which is incorporated herein by reference.

While Scheme (I) illustrates certain $Dab^9$ derivatives of the invention in which substituent $R^6$ is attached to the macrocyclic $Dab^9$ residue via an amide linkage, those of skill in the art will recognize that $Dab^9$ derivatives including other linkages may be synthesized by routine modification of the illustrated schemes. Moreover, in some instances, substituent $R^6$ may include additional functionalities requiring protection. The identity of the protecting group will depend upon, among other things, the functionality being protected and other protecting groups present on the molecule, and will be apparent to those of skill in the art. Guidance may be found in Greene & Wuts, supra.

The $Dab^9$ derivatives of the invention may be isolated and purified using standard techniques such as high performance liquid chromatography, counter current extraction, centrifugation, filtration, precipitation, ion exchange chromatography, gel electrophoresis, affinity chromatography, etc. Specific methods of isolation are provided in the Examples section, infra. Any of the various parent antibiotics, reaction, intermediates and/or $Dab^9$ derivatives of the invention may also be isolated and purified using the extractive purification methods described in application Ser. No. 60/286,254, filed Apr. 24, 2001, which is incorporated herein by reference.

Those of skill in the art will appreciate that many of the $Dab^9$ derivatives of the invention, as well as the various compound species specifically described herein, may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

Moreover, although the exact optical configurations of the chiral centers of the various illustrated amphomycin-type macrocyclic cores are not specified, it is to be understood that the structural illustrations are intended to be a shorthand way of describing these cores, and are not intended to be limiting. It will be understood that the specific optical configurations are those possessed by the macrocyclic cores of the amphomycin-type lipopeptide antibiotics, whether they are known or unknown.

Also, while these structures of the peptide macrocycles comprising the various parent amphomycin-type lipopeptide antibiotics from which the $Dab^9$ derivatives of the invention are derived are believed to be correct, in some instances at a later date, errors may be revealed. Again, the structural illustrations are intended to be a short-hand way of describing the various compounds and are not intended to be limiting. It will be understood that in the $Dab^9$ derivatives of the invention, the structures of the peptide macrocycles are those possessed by the parent amphomycin-type lipopeptide antibiotics from which the specific derivatives are derived.

Antimicrobial Activity

The $Dab^9$ derivatives of the invention generally exhibit antimicrobial activity against Gram-positive bacteria that is similar to that exhibited by conventional amphomycin-type lipopeptide antibiotics, as measured in in vitro assays. Moreover, many of the $Dab^9$ derivatives of the invention may display improved therapeutic potential, such as reduced toxicity, as compared with conventional amphomycin-type lipopeptide antibiotics, making the $Dab^9$ derivatives of the invention particularly suited for systemic administration to combat infections caused by Gram-positive bacteria.

Generally, active $Dab^9$ derivatives of the invention are identified using conventional in vitro screening assays such as standard NCCLS bacterial inhibition assays, or MIC tests. See, e.g., National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically—Third Edition," Approved Standard M7-A3, National Committee for Clinical Standards, Villanova, Pa. ("Approved Standard M-7-A3"). Compounds considered active will typically exhibit MICs of less than about 64 µg/mL, usually less than about 32 µg/mL, preferably less than about 16 µg/mL and most preferably less than about 4 µg/mL against Gram-positive bacterial such as Strepto-, Staphylo- and *Enterococci* in these standard assays. Of course, compounds having MICs on the low end of these ranges, or even lower, are preferred. Most preferred for use in treating or preventing systemic infections are $Dab^9$ derivatives that exhibit significant antimicrobial activity (i.e., less than 4 µg/mL) and low toxicity. Systemic toxicity is less of a concern for topical administration. Specific assays suitable for demonstrating antimicrobial activity are provided in the Examples section.

Uses and Compositions

The antimicrobial $Dab^9$ derivatives of the invention can be used in a wide variety of applications to inhibit the growth of or kill microorganisms. For example, the antimicrobial $Dab^9$ derivatives may be used as disinfectants or as preservatives for materials such as foodstuffs, cosmetics, medicaments and other nutrient containing materials. The antimicrobial $Dab^9$ derivatives can also be used to treat or prevent diseases related to or caused by microbial infection in subjects such as plants and animals, including humans.

For use as a disinfectant or preservative, the antimicrobial $Dab^9$ derivatives can be added to the desired material singly, as mixtures of antimicrobial $Dab^9$ derivatives, or in combination with other antifungal and/or antimicrobial agents. The antimicrobial $Dab^9$ derivatives may be supplied as the compound per se or may be in mixture or admixture with a variety of pharmaceutically acceptable carriers, diluents or excipients, which are well known in the art.

When used to treat or prevent microbial infections or diseases related thereto, the antimicrobial $Dab^9$ derivatives of the invention can be administered or applied singly, as mixtures of two or more antimicrobial $Dab^9$ derivatives, in combination with other antifungal, antibiotic or antimicrobial agents or in combination with other pharmaceutically active agents. The antimicrobial $Dab^9$ derivatives can be administered or applied per se or as pharmaceutical compositions. The specific pharmaceutical formulation will depend upon the desired mode of administration, and will be apparent to those having skill in the art. Numerous compositions for the topical or systemic administration of antibiotics are described in the literature. Any of these compositions may be formulated with the antimicrobial $Dab^9$ derivatives of the invention.

Pharmaceutical compositions comprising the antimicrobial $Dab^9$ derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active antimicrobial $Dab^9$ derivatives into preparations which can be used pharmaceutically. Proper formulation is dependent upon the route of administration chosen.

For topical administration the antimicrobial $Dab^9$ derivatives of the invention may be formulated as solutions, gels, ointments, creams, suspensions, pastes, and the like, as are well-known in the art.

Systemic formulations include those designed for administration by injection, e.g. subcutaneous, intravenous, intramuscular, intrathecal or intraperitoneal injection, as well as those designed for transdermal, transmucosal, oral, or pulmonary administration. In a preferred embodiment, the systemic formulation is sterile.

For injection, the antimicrobial $Dab^9$ derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the antimicrobial $Dab^9$ derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the antimicrobial $Dab^9$ derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In a preferred embodiment, the aerosol composition is sterile. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The antimicrobial $Dab^9$ derivatives may also be formulated in rectal or vaginal compositions such as suppositories or retention enemas, e.g., containing conventional suppository bases such as cocoa butter or other glycerides.

In addition to the formulations described previously, the antimicrobial $Dab^9$ derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the antimicrobial $Dab^9$ derivatives of the invention. Certain organic solvents such as dimethylsulfoxide also may be employed, although usually at the cost of greater toxicity. Additionally, the antimicrobial $Dab^9$ derivatives may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days.

As certain of the carboxyl groups of the antimicrobial $Dab^9$ derivatives of the invention are acidic, and/or the substituent $R^6$ may include acidic or basic substituents, the antimicrobial $Dab^9$ derivatives may be included in any of the above-described formulations as the free acids, the free bases or as pharmaceutically acceptable salts. Pharmaceutically acceptable salts are those salts which retain substantially the antimicrobial activity of the free acids or bases and which are prepared by reaction with bases or acids, respectively. Suitable acids and bases are well known to those of skill in the art. Pharmaceutical salts tend to be more soluble in aqueous and other protic solvents than are the corresponding free-base or acid forms.

The antimicrobial $Dab^9$ derivatives of the invention, or compositions thereof, will generally be used in an amount effective to achieve the intended purpose. Of course, it is to be understood that the amount used will depend on the particular application.

For example, for use as a disinfectant or preservative, an antimicrobially effective amount of an antimicrobial $Dab^9$ derivative or composition thereof is applied or added to the material to be disinfected or preserved. By "antimicrobial effective amount" is meant an amount of an antimicrobial $Dab^9$ derivative or composition that inhibits the growth of, or is lethal to, a target microbe. While the actual amount will depend on the particular target microbe and application, for use as a disinfectant or preservative, the antimicrobial $Dab^9$ derivatives, or compositions thereof, are usually added or applied to the material to be disinfected or preserved in relatively low amounts. Typically, the antimicrobial $Dab^9$ derivatives comprise less than about 5% by weight of the disinfectant solution or material to be preserved, preferably less than about 1% by weight and more preferably less than about 0.1% by weight. An ordinarily skilled artisan will be able to determine antimicrobially effective amounts of particular antimicrobial $Dab^9$ derivatives for particular applications without undue experimentation using, for example, the in vitro assays discussed above.

For use to treat or prevent microbial infections, the antimicrobial $Dab^9$ derivatives of the invention, or compositions thereof, are administered or applied in a therapeutically effective amount. By "therapeutically effective amount" is meant an amount effective to ameliorate the symptoms of, or ameliorate, treat or prevent microbial infections. Determination of a therapeutically effective amount is well within the capabilities of those skilled in the art, especially in light of the detailed disclosure provided herein.

As in the case of disinfectants and preservatives, a therapeutically effective dose for topical administration to treat or prevent microbial infections can be determined using, for example, the in vitro assays discussed above. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating antimicrobial $Dab^9$ derivative concentration range that includes the MIC as determined in cell culture.

Initial dosages can also be estimated from in vivo data, e.g., animal models, using techniques that are well known in the art. One having ordinary skill in the art can readily optimize administration to humans based on animal data.

Alternatively, initial dosages can be determined from the dosages administered of known amphomycin-type lipopeptide antibiotics (e.g., amphomycin, aspartocin, crystallomycin, antibiotic A1437, friulimycin, glumamycin, tsushimycin and zaomycin) by comparing the MIC of the specific antimicrobial $Dab^9$ derivative with that of the known antimicrobial agent, and adjusting the initial dosages accordingly. The optimal dosage may be obtained from these initial values by routine optimization.

Dosage amount and interval may be adjusted individually to provide plasma levels of the active antimicrobial $Dab^9$ derivative that are sufficient to maintain a therapeutic effect. Usual patient dosages for administration by injection range from about 0.1 to 200 mg/kg/day, but more typically range from about 1.5 to 15 mg/kg/day. Therapeutically effective serum levels may be achieved by administering a single dose daily or multiple doses each day.

In cases of local administration or selective uptake, the effective local concentration of antimicrobial $Dab^9$ derivative may not be related to plasma concentration. One having skill in the art will be able to optimize therapeutically effective local dosages without undue experimentation.

The amount of antimicrobial $Dab^9$ derivative administered will, of course, be dependent on, among other factors, the subject being treated, the subject's weight, the severity of the affliction, the manner of administration and the judgment of the prescribing physician.

The antimicrobial therapy may be repeated intermittently while infections are detectable, or even when they are not detectable. The therapy may be provided alone or in combination with other drugs, such as for example other antibiotics or antimicrobials, or other antimicrobial $Dab^9$ derivatives of the invention.

Preferably, a therapeutically effective dose of the antimicrobial $Dab^9$ derivatives described herein will provide therapeutic benefit without causing substantial toxicity. Toxicity of the antimicrobial $Dab^9$ derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Antimicrobial $Dab^9$ derivatives that exhibit high therapeutic indices are preferred. The data obtained from these cell culture assays and animal studies can be used in formulating a dosage range that is not toxic for use in human subjects. The dosage of the antimicrobial $Dab^9$ derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition or need thereof (see, e.g. Fingl et al., 1975, *In: The Pharmacological Basis of Therapeutics*, Chapter 1).

The invention having been described, the following examples are intended to illustrate, and not limit, the invention.

EXAMPLES

Example 1

Compound Synthesis

A number of $Dab^9$ derivatives of aspartocin were prepared according to Scheme (I) from cultured aspartocin, both with and without prior separation and isolation of the various fatty acid fractions. In the nomenclature used herein, "$natC_{14}$" designates the isolated $C_{14}$ fatty acid fraction of the indicated compound and "$natC_{15}$" designates the isolated $C_{15}$ fatty acid fraction of the designated compound. The substituent $R^6$ attached to the β-amino group of the macrocyclic $Dab^9$ residue follows the name of the parent amphomycin-type lipopeptide antibiotic (in parentheses).

Fermentation of Aspartocin in a Bioreactor

The aspartocin complex was produced by fermentation in a 700-liter stainless steel bioreactor. Biochemical synthesis of aspartocin is performed by inoculating a medium composed of 1.0% dextrose, 0.5% molasses, 1.0% Bacto Peptone, and 0.1% $CaCO_3$ in 100 mL of tap water, with spore and mycelial scrapings from a slant of *Streptomyces griseus* ssp. *spiralis* (NRRL B-3290; BSP-M707). The inoculated medium is incubated at a temperature of about 28° C. on a rotary shaker at about 180 rotations per minute (RPM) for about 48 hours providing a substantial and uniform vegetative growth. This seed growth, 10 ml, was transferred to 400 ml of the same medium in a 2-liter flask which was incubated under the same conditions and then added to 9.6 liters of the same medium in a 16-liter fermentor to give the $3^{rd}$ stage seed after 48 hrs., 200 rpm, 5 Lpm air flow. This final seed stage was used to inoculate 500 liters of medium containing 1 g/L $CaCO_3$, 10 g/L Grandma's Molasses (unsulfered), 10 g/L Difco Bacto Peptone, and 20 g/L Baker Dextrose adjusted to pH 7.1 prior to sterilization. Fermentation was conducted with agitation speed 200 rpm, air flow 125 Lpm, and 28° C. with addition of antifoam, Mazu DF204, as required. Fermentation was harvested after 114 hours.

Process to Obtain Crude Preparation

The cells and other solids of the fermentation broth were removed by centrifugation and the supernatant, 470 L, was adjusted to pH 3.3 with HCl and allowed to stand at 14° C. for 2 hours. A precipitate was removed by centrifuge and discarded. The decant adjusted to pH 7.0 to which ammonium sulfate was added to cause precipitation of the crude antibiotic complex. The precipitate was separated by centrifugation, dissolved in water, adjusted to pH 7.0, and then freeze dried to obtain 2058 g of solid containing 5–7% of the aspartocin complex. Further purification was accomplished by the chelate procedure described below.

Extractive Purification of Aspartocin

A dark colored crude preparation, 68.3 grams, containing 5–7% of the aspartocin complex was dissolved in 500 ml distilled water and stirred as it was adjusted to pH 7.0 to obtain best water solubility. Some insoluble material was separated by centrifuge and the decant was adjusted to pH 3.5. The aspartocin complex was extracted by two sequential 1-butanol extractions (500 ml, 300 ml) and 600 ml of water were added to the combined butanol phases. The resulting two phase system was stirred and adjusted to pH 8.0 with 1 N NaOH to provide the aspartocin complex as the sodium salt in the aqueous phase. Calcium chloride (2.642 g) was added to the separated aqueous phase, and the aspartocin extracted into 1-butanol as a chelate by two sequential extractions (500 ml, 250 ml). To remove calcium, the 1-butanol phases were combined, mixed with 900 ml water, adjusted to pH 3.0, separated from the aqueous phase, and washed with 150 ml of water. The 1-butanol phase containing the aspartocin complex was combined with 500 ml water and adjusted to pH 7.0. To remove some residual pigments, the aqueous phase containing the antibiotic complex was adjusted to pH 3.0 and mixed with 500 ml of 1-butanol. The 1-butanol phase was separated, washed with 150 ml water (pH 2–3), and combined with 500 ml water and the mixture adjusted to pH 7.0. The aqueous phase containing the aspartocin complex as a partial sodium salt was evaporated under vacuum to remove residual 1-butanol and freeze-dried to obtain 3.6 g of a white powder. HPLC analysis of the purified complex showed that the aspartocin complex was approximately 90% pure by 215 nm area % with peaks of the complex between 9.4 to 10.6 minutes. The HPLC system utilized a Prodigy® 5μ ODS(2) column eluted with an eight minute gradient of 10% to 75% acetonitrile at pH 7.2 with 0.05 M phosphate buffer.

Synthesis of Aspartocin(Dab$^9$-N-Glycyl)

A solution of N-(9-Fluorenylmethoxycarbonyl)glycine (12.5 mg, 41.7 μmol) and O-benzotriazol-1-yl-N,N,N',N'-tetramethyluronium hexafluorophosphate ("HBTU"; 15.8 mg, 41.7 μmol) in 0.75 mL of DMF was stirred at ambient temperature for 1 hour. Aspartocin (50 mg, 37.9 μmol), prepared as described above, was added to the reaction mixture and stirred for 30 minutes, after which time all of the aspartocin was acylated as detected by ion spray mass spectrometry. Piperidine (0.2 mL) was added in one portion and the solution was stirred for 15 minutes. The reaction mixture was worked up by addition of saturated aqueous solution of ammonium chloride (1 mL) as well as methanol (2 mL). The mixture was filtered and purified by reverse phase HPLC (70:30–10:90 of A:B in which A=90% H$_2$O, 10% acetonitrile ("ACN"), 0.1% trifluoroacetic acid ("TFA") and B=90% ACN, 10% H$_2$O, 0.1% TFA) over 32 minutes with a flow rate of 6.0 mL/min using a C18 Hyperprep BDS column from National Scientific (150×20 mm). The aspartocin(Dab$^9$-N-glycyl) product eluted at approx. 30 minutes, with the C$_{14}$ fraction eluting at about 29 min. and the C$_{15}$ fraction eluting at about 29.5–30 min. Purity of each fraction from prep HPLC was further analyzed by reverse phase HPLC (100% A to 100% B in which A=90% ammonium phosphate buffer at pH=7.1, 10% ACN and B=85% ACN, 15% H$_2$O) at λ=214 nm using a hypersil column from National Scientific (250×4.6 mm) at 40° C. and only fractions higher than 95% purity were combined. [M+H]$^+$ calcd for C$_{62}$H$_{99}$N$_{14}$O$_{21}$, 1375.7; found 1375.7.

Synthesis of Additional Dab$^9$ Derivatives

Additional derivatives as specified in TABLE 1 were also synthesized. All acylations of aspartocin with amino acids were performed on 50 mg of aspartocin complex and the same ratio of the reagents as noted in Section 6.1.1, supra. In cases where the amino acid carries a t-butyl based protecting group, such as Fmoc-Ser(t-Bu)-OH, after removal of Fmoc, trifluoroacetic acid (2 mL) was added and the mixture was stirred overnight. The mixture was then filtered as described before and purified by prep HPLC.

Purification of the Dab$^9$ Derivatives

In general, the various Dab$^9$ derivatives of aspartocin have very similar retention times on prep as well as on analytical HPLC. On prep, most derivatives eluted at about 28 to 30 minutes and on analytical at about 13 to 14 minutes. Each fraction was tested by analytical HPLC for purity as well as by ion spray mass spectrometry for characterization. The natural product produced by fermentation contains a family of analogs of aspartocin with the C$_{15}$ fatty acid as the most abundant compound and the C$_{14}$ fatty acid as the second abundant compound, in addition to other analogs. The C$_{14}$ and C$_{15}$ fatty acid fractions were separated by prep HPLC as described in Section 6.1.2, supra, and submitted for MIC measurements as described below. The various compounds synthesized and tested, as well as their observed masses (M+H) as determined by mass spectrometry, are provided in Table 1.

Example 2

In Vitro Antimicrobial Activity

This Example demonstrates that the various Dab$^9$ aspartocin derivatives synthesized according to the previous example exhibit significant antimicrobial activity against Gram-positive bacteria in in vitro assays.

Determination of MIC

Minimum Inhibitory Concentrations (MICs) were determined in the presence and absence of calcium according to the protocol described in Approved Standard M7-A3, supra. For measurements carried out in the presence of calcium, 4 mM CaCl$_2$ was added to the media at the beginning of the assay.

Results

The results of the various assays are tabulated in TABLE 1, below. As can be seen from TABLE 1, the presence of primary and secondary amines spaced about 3–6 carbons from the Dab$^9$ β-amine improves the activity of these antimicrobial compounds. Amino acid side chains are well tolerated and do not appear to decrease the antimicrobial activity of the compounds.

TABLE 1

| Compound No. | Name | MIC(μg/mL)[1] w/Ca$^{2+}$ | MIC(μg/mL)[1] w/o Ca$^{2+}$ | ED$_{50}$ | Mass Calcd | Mass Observed (M + H) |
|---|---|---|---|---|---|---|
| IB-756 | Aspartocin | 2 | 1 | 3 | | |
| IB-1272 | NatC$_{15}$-aspartocin(Dab$^9$-N-glycyl) | 0.8 | 0.7 | 1.8 | 1374.7 | 1375.7 |
| IB-1274 | NatC$_{14}$-aspartocin(Dab$^9$-N-L-alanyl) | 32 | 2 | | 1374.7 | 1375.8 |
| IB-1275 | NatC$_{15}$-aspartocin(Dab$^9$-N-L-alanyl) | 16 | 1 | 15.7 | 1388.7 | 1389.8 |
| IB-1278 | NatC$_{15}$-aspartocin(Dab$^9$-N-β-alanyl) | 2 | 2 | | 1388.7 | 1389.8 |
| IB-1279 | NatC$_{15}$-aspartocin(Dab$^9$-N-D-alanyl) | 2 | 1 | 6 | 1388.7 | 1389.8 |
| IB-1280 | NatC$_{14}$-aspartocin(Dab$^9$-N-D-alanyl) | 4 | 0.5 | | 1374.7 | 1375.8 |
| IB-1281 | NatC$_{15}$-aspartocin(Dab$^9$-N-L-seryl) | 16 | 1 | 14.7 | 1404.7 | 1405.8 |
| IB-1282 | NatC$_{15}$-aspartocin(Dab$^9$-N-L-lysyl) | 8 | 0.5 | | 1445.8 | 1446.8 |
| IB-1303 | NatC$_{15}$-aspartocin(Dab$^9$-N-scarcosyl) | 1 | 1.3 | | 1388.7 | 1389.7 |
| IB-1305 | NatC$_{14}$-aspartocin(Dab$^9$-N-γ-aminobutyryl) | | | | 1388.7 | 1389.7 |
| IB-1307 | NatC$_{15}$-aspartocin(Dab$^9$-N-γ-aminobutyryl) | 2 | 0.5 | | 1402.7 | 1403.7 |
| IB-1308 | NatC$_{15}$-aspartocin(Dab$^9$-N-glycyl) | 2 | 2 | | 1360.7 | 1361.7 |
| IB-1312 | NatC$_{15}$-aspartocin(Dab$^9$-N-histidyl) | 10.7 | 1.7 | | 1459.7 | 1455.7 |

[1]All MICs are the average of three datapoints.

Example 3

In Vivo Efficacy

The in vivo efficacy of the compounds of the invention was demonstrated with compound 1272 in a mouse protection model.

Protocol

Preparation of Inoculum

An overnight culture of methicillin sensitive *Staphylococcus aureus* ("MSSA"; Smith strain) grown to stationary phase in brain heart infusion broth (BHI) was diluted 1000-fold and maintained at 37° C. in a shaking incubator. Approximately two hours later the culture was centrifuged and the pellet was washed with sterile phosphate-buffered saline ("PBS"). The washed pellet was then reconstituted in Mueller-Hinton Broth ("MHB") to achieve the desired density of bacteria. A portion of the inoculum was plated on blood agar plates to determine colony-forming units (CFU) per milliliter.

Formulation

Compound IB-1272 was formulated immediately before dosing in aqueous vehicle containing 5% dextrose. Compound IB-756 (Aspartocin) was formulated in PBS or 5% dextrose and used as a positive control.

Regimen

Immunocompetent Swiss Webster Mice from Simonsen Laboratories, Gilroy, Calif., received via intraperitoneal injection a single inoculum (0.5 ml) containing an estimated 4.0×10$^7$ CFU of MSSA Smith strain. The day of inoculation was designated study day 0. Immediately after infection, mice were treated subcutaneously with a single dose of vehicle alone, IB-1272 (2, 4, or 8 mg/kg), IB-756 (2.5 or 5 mg/kg in PBS), or IB-756 (2.5 or 5 mg/kg in 5% dextrose). A detailed description of the group assignments is presented in Table 2.

TABLE 2

| Group | Predicted CFU/mouse | Actual CFU/mouse[a] | Number of Mice | Test Article | Conc. (mg/ml) | Dose Volume (ml/kg) | Dosage (mg/kg) |
|---|---|---|---|---|---|---|---|
| 1 | 4.0 × 10$^7$ | 3.56 × 10$^7$ | 11 | Vehicle | 0 | 4 | 0 |
| 2 | 4.0 × 10$^7$ | 3.56 × 10$^7$ | 10 | IB-756 (in PBS) | 0.63 | 4 | 2.5 |
| 3 | 4.0 × 10$^7$ | 3.56 × 10$^7$ | 10 | IB-756 (in PBS) | 1.25 | 4 | 5.0 |
| 4 | 4.0 × 10$^7$ | 3.56 × 10$^7$ | 10 | IB-756 (in 5% dextrose) | 0.63 | 4 | 2.5 |
| 5 | 4.0 × 10$^7$ | 3.56 × 10$^7$ | 10 | IB-756 (in 5% dextrose) | 1.25 | 4 | 5.0 |
| 6 | 4.0 × 10$^7$ | 3.56 × 10$^7$ | 10 | IB-1272 | 0.5 | 4 | 2.0 |
| 7 | 4.0 × 10$^7$ | 3.56 × 10$^7$ | 10 | IB-1272 | 1.0 | 4 | 4 |
| 8 | 4.0 × 10$^7$ | 3.56 × 10$^7$ | 10 | IB-1272 | 2.0 | 4 | 8 |

[a]Actual CFU obtained from plate counts of the inoculum.

RESULTS

Survival data are summarized in TABLE 3. Mortality in the vehicle-control mice was 100%. Mortality among mice treated subcutaneously with IB-756 (formulated in PBS) at doses of 2.5 or 5 mg/kg was 60% and 0%, respectively. Mortality among mice treated subcutaneously with IB-756 (formulated in 5% dextrose) at doses of 2.5 or 5 mg/kg was 50% and 0%, respectively. Mortality among mice treated subcutaneously with IB-1272 at doses of 2, 4, or 8 mg/kg was 50%, 0% and 0%, respectively.

The $ED_{50}$ for subcutaneously administered IB-1272 was <2.0 mg/kg in immunocompetent mice challenged intraperitoneally with MSSA Smith strain. The efficacy of IB-756 (aspartocin) was the same when formulated in 5% dextrose or in PBS.

TABLE 3

Survival of Immunocompetent Mice infected Intraperitoneally with MSSA and Dosed Subcutaneously with IB-1272

| Group | Compound | Actual CFU/Mouse | Dosage (mg/kg) | Number of Mice | Number Dead | Percent Mortality | Percent Survival |
|---|---|---|---|---|---|---|---|
| 1 | None | $3.56 \times 10^7$ | 0 (vehicle) | 11 | 11 | 100 | 0 |
| 2 | IB-756 (in PBS) | $3.56 \times 10^7$ | 2.5 | 10 | 6 | 60 | 40 |
| 3 | IB-756 (in PBS) | $3.56 \times 10^7$ | 5.0 | 10 | 0 | 0 | 100 |
| 4 | IB-756 (in 5% dextrose) | $3.56 \times 10^7$ | 2.5 | 10 | 5 | 50 | 50 |
| 5 | IB-756 (in 5% dextrose) | $3.56 \times 10^7$ | 5.0 | 10 | 0 | 0 | 100 |
| 6 | IB-1272 | $3.56 \times 10^7$ | 2.0 | 10 | 5 | 50 | 50 |
| 7 | IB-1272 | $3.56 \times 10^7$ | 4 | 10 | 0 | 0 | 100 |
| 8 | IB-1272 | $3.56 \times 10^7$ | 8 | 10 | 0 | 0 | 100 |

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. An antimicrobial compound according to structural formula (III):

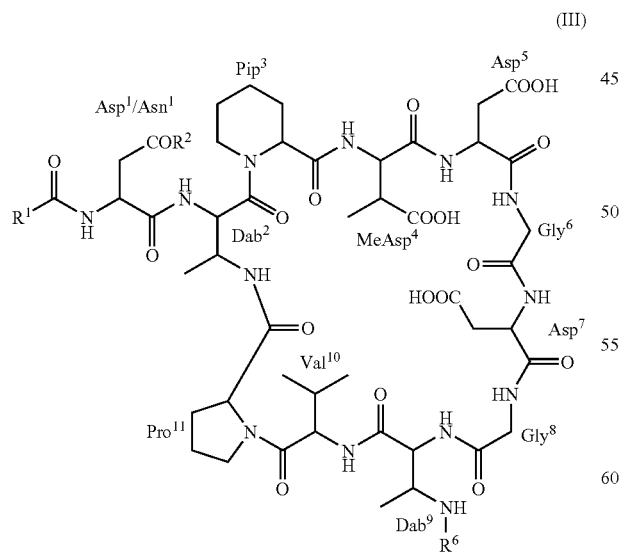

or pharmaceutically acceptable salt thereof, wherein:

$R^3$ is independently selected from hydrogen, $(C_1-C_{25})$ alkyl optionally substituted with one or more of the same or different $R^{15}$ groups, $(C_1-C_{25})$ heteroalkyl optionally substituted with one or more of the same or different $R^{15}$ groups, $(C_5-C_{10})$ aryl optionally substituted with one or more of the same or different $R^{15}$ groups, $(C_5-C_{15})$ arylaryl optionally substituted with one or more of the same or different $R^{15}$ groups, $(C_5-C_{15})$ biaryl optionally substituted with one or more of the same or different $R^{15}$ groups, 5–10 membered heteroaryl optionally substituted with one or more of the same or different $R^{15}$ groups, $(C_6-C_{26})$ arylalkyl optionally substituted with one or more of the same or different $R^{15}$ groups, 6–26 membered heteroarylalkyl optionally substituted with one or more of the same or different $R^{15}$ groups, and a linear or branched, saturated or singly or multiply unsaturated alkyl or hydroxy alkyl having a chain of 6 to 22 carbon atoms;

$R^4$ is Asp or Asn;

$R^6$ is independently selected from at least one amino acid, a substituent comprising a primary or secondary amine, $(C_1-C_{25})$ alkyl optionally substituted with one or more of the same or different $R^{15}$ groups, $(C_1-C_{25})$ heteroalkyl optionally substituted with one or more of the same or different $R^{15}$ groups, $(C_5-C_{10})$ aryl optionally substituted with one or more of the same or different $R^{15}$ groups, $(C_5-C_{15})$ arylaryl optionally substituted with one or more of the same or different $R^{15}$ groups, $(C_5-C_{15})$ biaryl optionally substituted with one or more of the same or different $R^{15}$ groups, 5–10 membered heteroaryl optionally substituted with one or more of the same or different $R^{15}$ groups, $(C_6-C_{26})$ arylalkyl optionally substituted with one or more of the same or different $R^{15}$ groups, and 6–26 membered heteroarylalkyl optionally substituted with one or more of the same or different $R^{15}$ groups;

each $R^{15}$ is independently selected from $-OR^{16}$, $-SR^{16}$, $NR^{16}R^{16}$, $-CN$, $-NO_2$, $-N_3$, $-C(O)OR^{16}$, $-C(O)NR^{16}R^{16}$, $-C(S)NR^{16}R^{16}$, $-C(NR^{16})NR^{16}R^{16}$, $-CHO$, $-R^{16}CO$, $-SO_2R^{16}$, $-SOR^{16}$, $-PO(OR^{16})_2$, $-PO(OR^{16})$, $-CO_2H$, $-SO_3H$, $-PO_3H$, halogen, and trihalomethyl; and each $R^{16}$ is independently selected from hydrogen, $(C_1-C_6)$ alkyl, $(C_5-C_{10})$ aryl, 5–10 membered heteroaryl, $(C_6-C_{16})$ arylalkyl, and 6–16 membered heteroarylalkyl.

2. The compound of claim 1 wherein $R^4$ is Asp.

3. The compound of claim 1 wherein $R^4$ is Asn.

4. The compound of claim 1 wherein $R^3$ is a linear saturated or singly unsaturated alkyl of 10 to 15 carbon atoms.

5. The compound of claim 1 wherein $R^3$ is a branched saturated or singly unsaturated alkyl of 10 to 15 carbon atoms.

6. The compound of claim 5 wherein the alkyl is in the iso or ante-iso configuration.

7. The compound of claim 1 wherein $R^6$ is at least one amino acid that is linked to the β-amino group of the macrocyclic $Dab^9$ residue via its carboxyl group, and wherein said at least one amino acid optionally includes a side chain moiety.

8. The compound of claim 1 in which $R^6$ has a $-X-R^{10}-NHR^7$ or a $-X-(CR^{11}R^{11})_n-NHR^7$ structure, wherein:

X is $-C(O)-$, $-C(O)O-$, $-CO(NH)-$, or $-S(O)_2-$;

$R^7$ is hydrogen or $(C_1-C_4)$ alkyl;

$R^{10}$ is independently selected from $-CH_2-$, $-CH=CH-$, $-C\equiv C-$, $-O-$, $-S-$, $-NH-$, $-NH-NH-$, $-N=N-$, $-C(O)-$, $-S(O)_2-$, $-S(O)_2-O-$, $-C(NH)-$, $(C_1-C_6)$ alkyldiyl, $(C_1-C_6)$ alkyleno, and $(C_1-C_6)$ alkano, wherein each $R^{10}$ is optionally substituted with $-NR^8R^8$, $-OR^8$, $-SR^8$, halogen, trihalomethyl, $-CN$, $-C(O)R^8$, $-C(O)OR^8$, $-C(O)NR^8R^8$, amidine, guanidine, alkyl optionally substituted with one or more of the same or different $R^9$, aryl optionally substituted with one or more of the same or different $R^9$, arylalkyl optionally substituted with one or more of the same or different $R^9$, heteroalkyl optionally substituted with one or more of the same or different $R^9$, and heteroarylalkyl optionally substituted with one or more of the same or different $R^9$;

each $R^8$ is independently selected from hydrogen, alkyl, aryl, arylalkyl, heteroaryl and heteroarylalkyl; and each $R^9$ independently selected from $-NR^8R^8$, $-OR^8$, $-SR^8$, halogen, trihalomethyl, $-CN$, $-C(O)R^8$, $-C(O)OR^8$, $-C(O)NR^8R^8$, amidine, guanidine, alkyl, aryl, arylalkyl, heteroaryl, and heteroarylalkyl;

each $R^{11}$ is independently selected from hydrogen, amino, amido, amidino, carboxy, guandino, hydroxy, sulfanyl, $(C_1-C_4)$ alkyl, $(C_1-C_4)$ alkyl substituted with one or more of the same or different $R^{12}$, $(C_5-C_{10})$ aryl, $(C_5-C_{10})$ aryl substituted with one or more of the same or different $R^{12}$, $(C_6-C_{13})$ arylalkyl, $(C_6-C_{13})$ arylalkyl substituted with one or more of the same or different $R^{12}$, 5–10 membered heteroaryl, 5–10 membered heteroaryl substituted with one or more of the same or different $R^{12}$, 6–13 membered heteroarylalkyl, and 6–13 membered heteroarylalkyl substituted with one or more of the same or different $R^{12}$;

each $R^{12}$ is independently selected from amino, amido, amidino, carboxyl, guanidino, hydroxy, and sulfanyl; and n is an integer from 1 to 6.

9. The compound of claim 8 wherein $R^{10}$ is independently selected from $(C_1-C_6)$ alkyldiyl, $(C_1-C_6)$ alkyleno, and $(C_1-C_6)$ alkano.

10. The compound of claim 8 wherein n is 1 and $R^{11}$ is a side-chain moiety of a genetically encoded amino acid.

11. The compound of claim 8 wherein n is 2 to 4 and only one $R^{11}$ is other than hydrogen.

12. The compound of claim 1 in which $R^6$ has a $-X^1-R^3$ structure, wherein $X^1$ is selected from $-CO-$, $-SO_2-$, $-CS-$, $-PO-$, $-OPO-$, $-OC(O)-$, $-NHCO-$, and $-NR^3CO-$.

13. The compound of claim 1 in which $R^4$ is attached to $R^3$ via a linker $X^1$, wherein $X^1$ is selected from $-CO-$, $-SO_2-$, $-CS-$, $-PO-$, $-OPO-$, $-OC(O)-$, $-NHCO-$, and $-NR^3CO-$.

14. The compound of claim 1 in which $R^6$ has a $-X^1-R^3$ structure and in which $R^4$ is attached to $R^3$ via a linker $X^1$, wherein $X^1$ is selected from $-CO-$, $-SO_2-$, $-CS-$, $-PO-$, $-OPO-$, $-OC(O)-$, $-NHCO-$, and $-NR^3CO-$.

15. A pharmaceutical composition comprising at least one compound according to one of claims 1, 8, and 12–14 and a pharmaceutically acceptable carrier, excipient or diluent.

16. A method of inhibiting the growth of Gram-positive bacteria, comprising contacting the bacteria with a compound according to claim 1 in an amount effective to inhibit growth.

17. The method of claim 16 wherein the compound is provided in an amount effective to kill Gram-positive bacteria.

18. The method of claim 16 or 17 wherein the Gram-positive bacteria are selected from *Streptococci* species, *Staphylococci* species, or *Enterococci* species.

19. A method of treating or preventing an infection caused by or associated with Gram-positive bacteria, comprising administering to a subject in need thereof at least one compound according to any one of claims 1, 8, and 12–14 in an amount effective to treat or prevent an infection caused by or associated with Gram-positive bacteria.

20. The method of claim 19 wherein said at least one compound is administered topically or systemically.

21. The method of claim 19 wherein the Gram-positive bacteria are selected from *Streptococci* species, *Staphylococci* species, or *Enterococci* species.

22. A method of treating or preventing an infection caused by or associated with Gram-positive bacteria, comprising administering to a subject in need thereof a composition according to claim 15 in an amount effective to treat or prevent an infection caused by or associated with Gram-positive bacteria.

23. The method of claim 22 wherein the composition is administered topically or systemically.

24. The method of claim 23 wherein the composition administered topically is in the form of a gel, ointment, cream, or paste.

25. The method of claim 22 wherein the Gram-positive bacteria are selected from *Streptococci* species, *Staphylococci* species, or *Enterococci* species.

* * * * *

UNITED STATES PATENT AND TRADEMARK OFFICE
CERTIFICATE OF CORRECTION

PATENT NO. : 7,125,844 B2
APPLICATION NO. : 10/336641
DATED : October 24, 2006
INVENTOR(S) : Maria Fardis et al.

It is certified that error appears in the above-identified patent and that said Letters Patent is hereby corrected as shown below:

Title Page Col. 2 (Other Publications); Line 6; Delete "Daptomyclm" and insert -- Daptomycin --, therefor.

Title Page Col. 2 (Other Publications); Line 24; Delete "antibiotice" and insert -- antibiotic --, therefor.

Column 1; Line 38; After "(glumamycin)" insert -- ( --.

Column 2; Line 63 (Approx); Delete "$NR_{16}R^{16}$," and insert -- $NR^{16}R^{16}$, --, therefor.

Column 2; Line 65; After "$-R^{16}CO, -SO_2R^{16}$," delete "$-SO_2R^{16}$," and insert-- $-SOR^{16}$, --, therefor.

Column 4; Line 24; Delete "sapcers" and insert -- spacers --, therefor.

Column 8; Line 66; Delete "heterorylalkynyl" and insert -- heteroarylalkynyl --, therefor.

Column 17; Line 46; Delete "eg.," and insert -- e.g., --, therefor.

Column 19; Line 21; After "heteroarylalkyl" insert -- . --.

Column 19; Line 33 (Approx.); Delete "antiobiotic" and insert -- antibiotic --, therefor.

Column 21; Line 45; Delete "(IIa)" and insert -- (IIIa) --, therefor.

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,125,844 B2
APPLICATION NO. : 10/336641
DATED : October 24, 2006
INVENTOR(S) : Maria Fardis et al.

It is certified that error appears in the above-identified patent and that said Letters Patent is hereby corrected as shown below:

Title Page Col. 2 (Other Publications); Line 6; Delete "Daptomyclm" and insert -- Daptomycin --, therefor.

Title Page Col. 2 (Other Publications); Line 24; Delete "antibiotice" and insert -- antibiotic --, therefor.

Column 1; Line 38; After "(glumamycin)" insert -- ( --.

Column 2; Line 63 (Approx); Delete "$NR_{16}R^{16}$," and insert -- $NR^{16}R^{16}$, --, therefor.

Column 2; Line 65; After "$-R^{16}CO, -SO_2R^{16}$," delete "$-SO_2R^{16}$," and insert-- $-SOR^{16}$, --, therefor.

Column 4; Line 24; Delete "sapcers" and insert -- spacers --, therefor.

Column 8; Line 66; Delete "heterorylalkynyl" and insert -- heteroarylalkynyl --, therefor.

Column 17; Line 46; Delete "eg.," and insert -- e.g., --, therefor.

Column 19; Line 21; After "heteroarylalkyl" insert -- . --.

Column 19; Line 33 (Approx.); Delete "antiobiotic" and insert -- antibiotic --, therefor.

Column 21; Line 45; Delete "(IIa)" and insert -- (IIIa) --, therefor.

Column 24 (Scheme 1); Line 3 (Approx.); Delete " 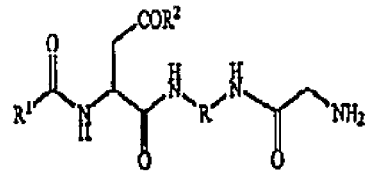 "

and insert -- 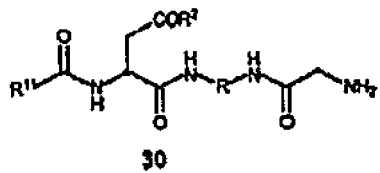 --, therefor.

Column 25; Line 11; Delete "Synthesis." and insert -- Synthesis: --, therefor.

UNITED STATES PATENT AND TRADEMARK OFFICE
CERTIFICATE OF CORRECTION

PATENT NO. : 7,125,844 B2
APPLICATION NO. : 10/336641
DATED : October 24, 2006
INVENTOR(S) : Maria Fardis et al.

It is certified that error appears in the above-identified patent and that said Letters Patent is hereby corrected as shown below:

Column 25; Line 12; Delete "reference)." and insert -- reference. --, therefor.

Column 38; Line 27 (Approx.); Delete "Mice" and insert -- mice --, therefor.

Column 39; Line 45-63 (Approx.); In Claim 1, delete

"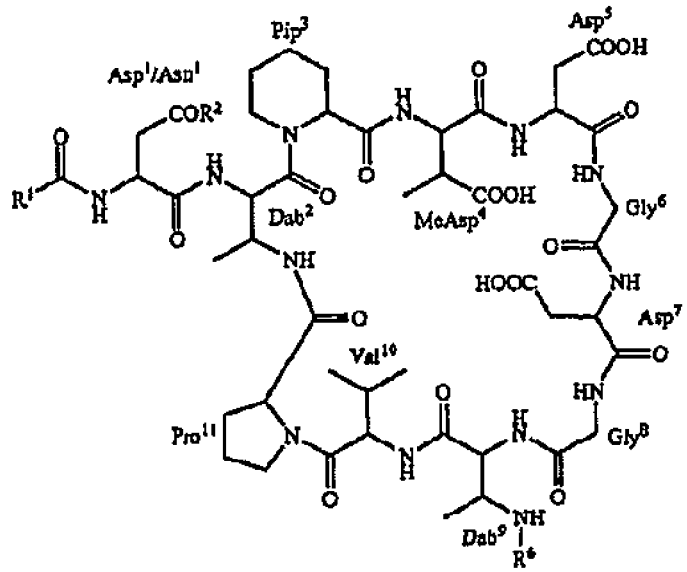"

and insert --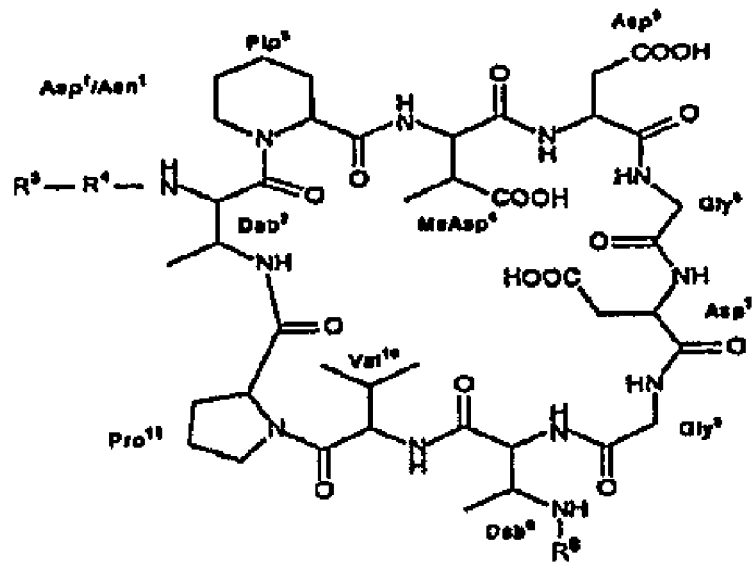--, therefor.

UNITED STATES PATENT AND TRADEMARK OFFICE
CERTIFICATE OF CORRECTION

PATENT NO. : 7,125,844 B2
APPLICATION NO. : 10/336641
DATED : October 24, 2006
INVENTOR(S) : Maria Fardis et al.

It is certified that error appears in the above-identified patent and that said Letters Patent is hereby corrected as shown below:

Column 41; Line 38; In Claim 8, after "each $R^9$" insert -- is --.

This certificate supersedes Certificate of Correction issued April 17, 2007.

Signed and Sealed this

Twenty-eighth Day of August, 2007

JON W. DUDAS
*Director of the United States Patent and Trademark Office*